(12) United States Patent
De la Brouse-Elwood et al.

(10) Patent No.: US 6,620,827 B2
(45) Date of Patent: *Sep. 16, 2003

(54) PPARγ MODULATORS

(75) Inventors: Fabienne De la Brouse-Elwood, San Francisco, CA (US); Jin-Long Chen, Millbrae, CA (US); Timothy D. Cushing, Pacifica, CA (US); John A. Flygare, Burlingame, CA (US); Jonathan B. Houze, San Mateo, CA (US); Juan C. Jaen, Burlingame, CA (US); Lawrence R. McGee, Pacifica, CA (US); Shi-Chang Miao, Foster City, CA (US); Steven Marc Rubenstein, Pacifica, CA (US); Patrick C. Kearney, San Francisco, CA (US)

(73) Assignee: Tularik Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/741,415

(22) Filed: Dec. 19, 2000

(65) Prior Publication Data

US 2001/0027200 A1 Oct. 4, 2001

Related U.S. Application Data

(63) Continuation of application No. 09/234,327, filed on Jan. 20, 1999, now Pat. No. 6,200,995.
(60) Provisional application No. 60/073,042, filed on Jan. 29, 1998.

(51) Int. Cl.[7] ............... A61K 31/44; A61K 31/406; C07D 213/643; C07D 213/65; C07D 213/71
(52) U.S. Cl. ............... 514/347; 514/345; 514/351; 546/294; 546/295
(58) Field of Search .................. 514/347, 294, 514/295, 345, 351; 546/294, 295

(56) References Cited

U.S. PATENT DOCUMENTS

| | | | |
|---|---|---|---|
| 2,407,309 A | 9/1946 | Lott et al. ............. 564/86 |
| 3,034,955 A | 5/1962 | Frick et al. ............ 514/664 |
| 3,674,843 A | 7/1972 | Shen et al. ............ 562/430 |
| 3,686,192 A | 8/1972 | Moore et al. .......... 546/293 |
| 4,003,734 A | 1/1977 | Johnston .............. 504/257 |
| 4,013,621 A | 3/1977 | Knell ................... 524/169 |
| 4,061,642 A | 12/1977 | Fleckenstein et al. ... 546/291 |
| 4,218,237 A | 8/1980 | Nishiyama et al. ..... 504/256 |
| 4,289,876 A | 9/1981 | Algieri et al. ......... 546/332 |
| 4,499,304 A | 2/1985 | Gabrielsen et al. ..... 564/92 |
| 4,549,901 A | 10/1985 | James ................. 504/257 |
| 4,565,568 A | 1/1986 | Johnston et al. ....... 504/258 |
| 4,577,028 A | 3/1986 | Martin et al. .......... 546/345 |
| 4,670,045 A | 6/1987 | Ehr et al. ............. 504/251 |
| 4,731,090 A | 3/1988 | Boger et al. ........... 8/129.5 |
| 4,756,739 A | 7/1988 | Fuss et al. ............. 504/254 |
| 4,866,079 A | 9/1989 | Boger et al. ........... 514/346 |
| 4,946,854 A | 8/1990 | Maienfisch et al. ..... 514/346 |
| 4,952,235 A | 8/1990 | Andree et al. ......... 504/251 |
| 4,987,141 A | 1/1991 | Bushell et al. ......... 514/346 |
| 5,008,276 A | 4/1991 | Clough et al. ......... 514/335 |
| 5,070,096 A | 12/1991 | Mohrs et al. .......... 514/311 |
| 5,143,937 A | 9/1992 | Lang et al. ............ 514/603 |
| 5,151,428 A | 9/1992 | Sakamoto et al. ...... 514/277 |
| 5,304,532 A | 4/1994 | Munro et al. .......... 504/337 |
| 5,360,810 A | 11/1994 | Hayase et al. ......... 514/346 |
| 5,444,036 A | 8/1995 | Iwasaki et al. ......... 503/209 |
| 5,514,696 A | 5/1996 | Murugesan et al. .... 514/380 |
| 5,545,669 A | 8/1996 | Adams et al. .......... 514/562 |
| 5,610,320 A | 3/1997 | Yoshino et al. ......... 549/72 |
| 5,643,914 A | 7/1997 | Daines ................. 514/277 |
| 5,684,195 A | 11/1997 | Huang et al. ........... 564/90 |
| 5,716,993 A | 2/1998 | Ozaki et al. ........... 514/619 |
| 5,880,136 A | 3/1999 | Duggan et al. ......... 514/317 |
| 6,200,995 B1 * | 3/2001 | De La Brouse-Elwood et al. ......... 514/347 |

FOREIGN PATENT DOCUMENTS

| | | | |
|---|---|---|---|
| CH | 592 411 A | 10/1977 | |
| CH | 592 411 | 10/1977 | ............. 514/345 |
| DE | 36 32 329 A | 3/1988 | |
| DE | 3632329 A1 | 3/1988 | ............. 514/345 |
| EP | 0 148 730 A2 | 7/1985 | ............. 514/345 |
| EP | 0 306 222 A2 | 8/1989 | |
| JP | 55-79369 | 6/1980 | ............. 541/294 |
| JP | 64-6245 | 1/1989 | ............. 514/345 |
| WO | WO 95/01326 A | 1/1995 | |
| WO | WO 95/01326 | 1/1995 | ............. 514/345 |
| WO | WO 95/33461 | 12/1995 | |
| WO | WO 97 00857 A | 1/1997 | |
| WO | WO 97/30677 | 8/1997 | |
| WO | WO 97/30677 | 8/1997 | ............. 514/345 |
| WO | WO97/00857 | 9/1997 | ............. 514/345 |
| WO | WO 97/31907 A | 9/1997 | |
| WO | WO 97/31907 | 9/1997 | ............. 514/345 |
| WO | WO 97 36579 A | 10/1997 | |
| WO | WO 97/36579 | 10/1997 | ............. 514/345 |

OTHER PUBLICATIONS

Chemical Abstracts, vol. 67, No. 9, Aug. 28, 1967, Columbus, Ohio, United States; abstract No. 43516y, p. 4076; XP002099084; & 1. Badilescu: "Sythesis of some N–aryl– and N,N–dialkyl–p–chloro–benzensulfonamides" Rev. Chim., vol. 17, No. 11, 1966, pp. 705–706.

Chemical Abstracts, vol. 67, No. 9, Aug. 28, 1967 Columbus Ohio; abstract No. 43516y, p. 4076; XP002099084 & I. Badilescu: "Synthesis of some N–aryl– and N,N–dialkyl–p–chloro–benzenesulfonamides" Rev. Chim.(Bucharest) vol. 17, No. 11, 1966, pp. 705–706, see abstract.

* cited by examiner

*Primary Examiner*—Alan L. Rotman
*Assistant Examiner*—Raymond Covington
(74) *Attorney, Agent, or Firm*—Townsend and Townsend and Crew LLP

(57) ABSTRACT

Modulators of PPARγ activity are provided which are useful in pharmaceutical compositions and methods for the treatment of conditions such as type II diabetes and obesity.

33 Claims, 4 Drawing Sheets

PPARγ MODULATORS

CROSS-REFERENCE TO RELATED APPLICATION

This application is a continuation of U.S. Application Ser. No. 09/234,327, filed on Jan. 20, 1999 (now issued U.S. Pat. No. 6,200,995), which claims the benefit of U.S. Application Ser. No. 60/073,042, filed on Jan. 29, 1998, the disclosures of which are incorporated herein by reference in their entirety.

FIELD OF THE INVENTION

The present invention relates to compounds that modulate the PPARγ receptor and are useful in the diagnosis and treatment of type II diabetes (and complications thereof) and inflammatory disorders.

BACKGROUND OF THE INVENTION

The peroxisome proliferator-activated receptors (PPARs) are transducer proteins belonging to the steroid/thyroid/retinoid receptor superfamily. The PPARs were originally identified as orphan receptors, without known ligands, but were named for their ability to mediate the pleiotropic effects of fatty acid peroxisome proliferators. These receptors function as ligand-regulated transcription factors that control the expression of target genes by binding to their responsive DNA sequence as heterodimers with RXR. The target genes encode enzymes involved in lipid metabolism and differentiation of adipocytes. Accordingly, the discovery of transcription factors involved in controlling lipid: metabolism has provided insight into regulation of energy homeostasis in vertebrates,;and further provided targets for the development of therapeutic agents for disorders such as obesity, diabetes and dyslipidemia.

PPARγ is one member of the nuclear receptor superfamily of ligand-activated transcription factors and has been shown to be expressed in an adipose tissue-specific manner. Its expression is induced early during the course of differentiation of several preadipocyte cell lines. Additional research has now demonstrated that PPARγ plays a pivotal role in the adipogenic signaling cascade. PPARγ also regulates the ob/leptin gene which is involved in regulating energy homeostasis, and adipocyte differentiation which has been shown to be a critical step to be targeted for anti-obesity and diabetic conditions.

In an effort to understand the role of PPARγ in adipocyte differentiation, several investigators have focused on the identification of PPARγ activators. One class of compounds, the thiazolidinediones, which were known to have adipogenic effects on preadipocyte and mesenchymal stem cells in vitro, and antidiabetic effects in animal models of non-insulin-dependent diabetes mellitus (NIDDM) were also demonstrated to be PPARγ-selective ligands. More recently, compounds that selectively activate murine PPARγ were shown to possess in vivo antidiabetic activity in mice.

Despite the advances made with the thiazolidinedione class of antidiabetes agents, unacceptable side effects have limited their clinical use. Accordingly, there remains a need for potent, selective activators of PPARγ which will be useful for the treatment of NIDDM and other disorders related to lipid metabolism and energy homeostasis. Still further, compounds that block PPARγ activity would be useful for interfering with the maturation of preadipocytes into adipocytes and thus would be useful for the treatment of obesity and related disorders associated with undesirable adipocyte maturation. Surprisingly, the present invention provides compounds that are useful as activators as well as antagonists of PPARγ activity and compositions containing them, along with methods for their use.

BRIEF SUMMARY OF THE INVENTION

In one aspect, the present invention provides methods of modulating conditions which are mediated by PPARγ. The methods typically involve contacting the host with a PPARγ-modulating amount of a compound having the formula:

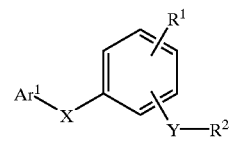

in which the symbol $Ar^1$ represents an aryl group; the letter X represents a divalent linkage selected from the group consisting of —($C_1$–$C_6$)alkylene, —($C_1$–$C_6$)alkylenoxy, —O—, —C(O)—, —N($R^{11}$)—, —N($R^{11}$)C(O)—, —S(O)$_k$— and a single bond, in which $R^{11}$ is a member selected from the group consisting of hydrogen, alkyl, heteroalkyl and arylalkyl and the subscript k is an integer of from 0 to 2. The letter Y, in the above formula represents a divalent linkage selected from the group consisting of alkylene, —O—, —C(O)—, —N($R^{12}$)—S(O)$_m$—, —N($R^{12}$)—S(O)$_m$—N($R^{13}$)—, —N($R^{12}$)C(O)—, —S(O)$_n$—, a single bond, and combinations thereof in which $R^{12}$ and $R^{13}$ are members independently selected from the group consisting of hydrogen, alkyl, heteroalkyl and arylalkyl; and the subscripts m and n are independently integers of from 0 to 2.

The symbol $R^1$ represents a member selected from the group consisting of hydrogen, alkyl, heteroalkyl, aryl, arylalkyl, —$CO_2R^{14}$, —C(O)$R^{14}$, —C(O)N$R^{15}R^{16}$, —S(O)$_p$—$R^{14}$, —S(O)$_q$—N$R^{15}R^{16}$, —O—C(O)—O$R^{17}$, —O—C(O)—$R^{17}$, —O—C(O)—N$R^{15}R^{16}$, —N($R^{14}$)—C(O)—N$R^{15}R^{16}$, —N($R^{14}$)—C(O)—$R^{17}$ and —N($R^{14}$)—C(O)—O$R^{17}$, in which $R^{14}$ is a member selected from the group consisting of hydrogen, alkyl, heteroalkyl, aryl and arylalkyl, and $R^{15}$ and $R^{16}$ are members independently selected from the group consisting of hydrogen, alkyl, heteroalkyl, aryl, and arylalkyl, or taken together with the nitrogen to which each is attached form a 5-, 6- or 7-membered ring. The symbol $R^{17}$ represents a member selected from the group consisting of alkyl, heteroalkyl, aryl and arylalkyl. Additionally, for the $R^1$ groups described above, the subscript p is an integer of from 0 to 3, and the subscript q is an integer of from 1 to 2.

The symbol $R^2$ represents a member selected from the group consisting of alkyl, heteroalkyl, aryl and arylalkyl.

In another aspect, the present invention provides compounds of the formula above, as well as pharmaceutical compositions containing the compounds described above.

DETAILED DESCRIPTION OF THE INVENTION

Figure 1:
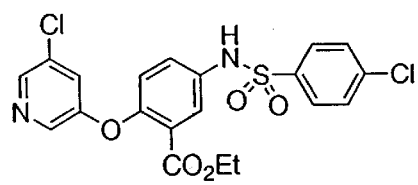
FIGS. 1–4 provide structures for a variety of compounds of the present invention.
Figure 1:
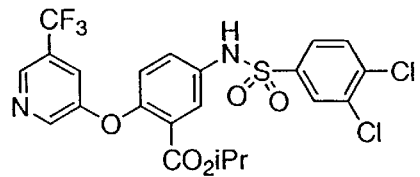
Figure 1:
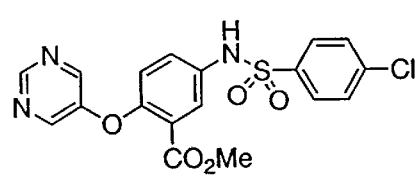
Figure 1:
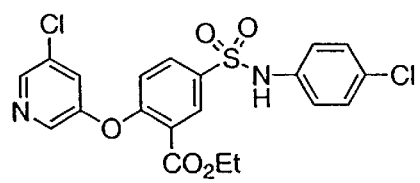
Figure 1:
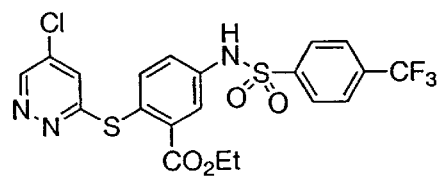
Figure 1:
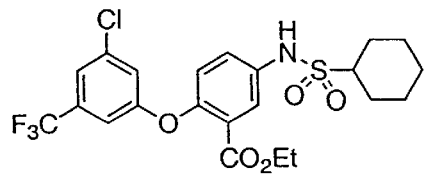
Figure 1:
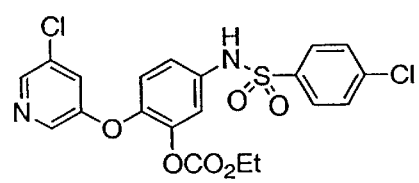
Figure 1:
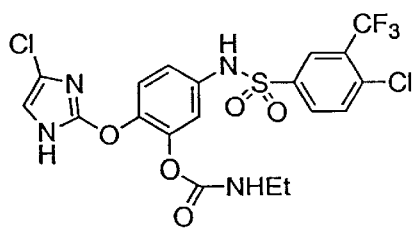
Figure 1:
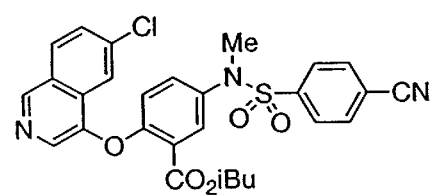
Figure 1:
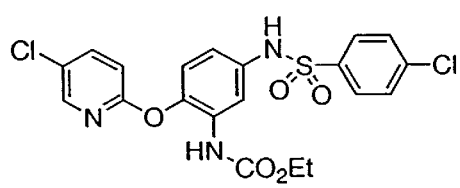
Figure 1:
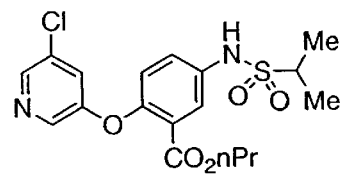
Figure 1:
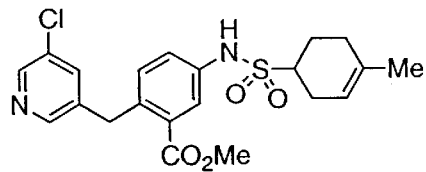
Figure 2:
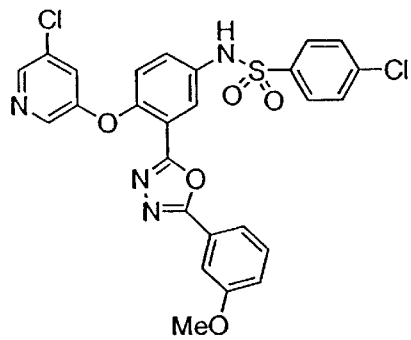
Figure 2:
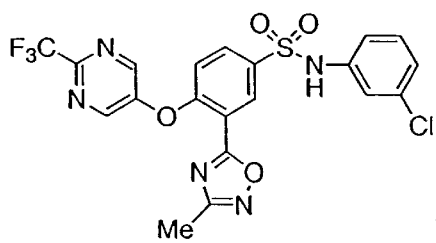
Figure 2:
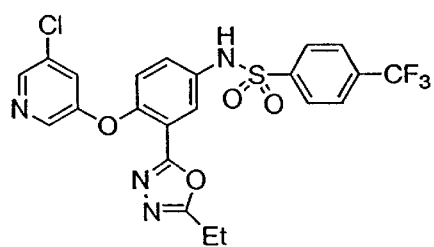
Figure 2:
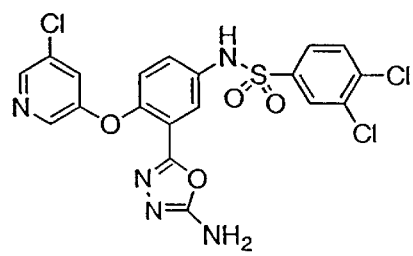
Figure 2:
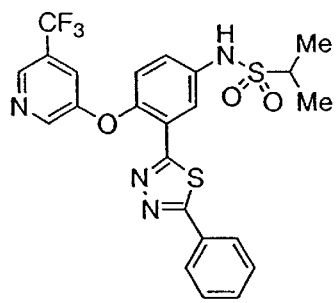
Figure 2:
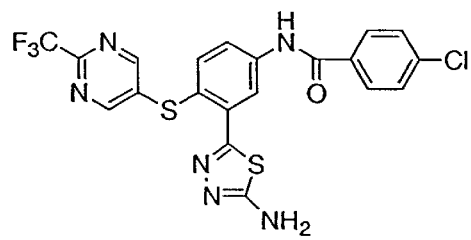
Figure 2:
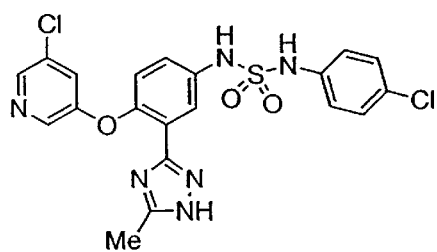
Figure 2:
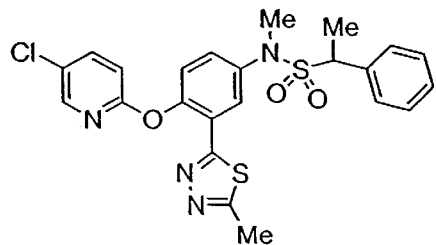
Figure 2:
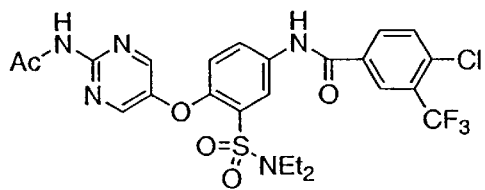
Figure 3:
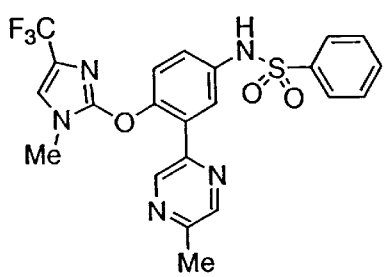
Figure 3:
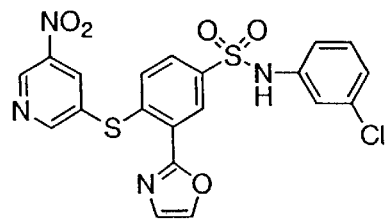
Figure 3:
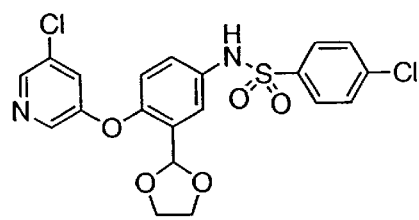
Figure 3:
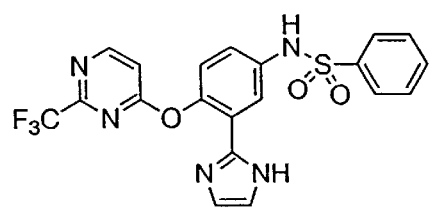
Figure 3:
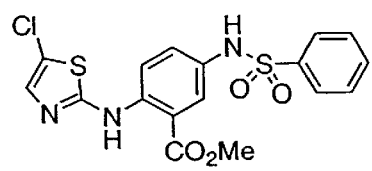
Figure 3:
Figure 3:
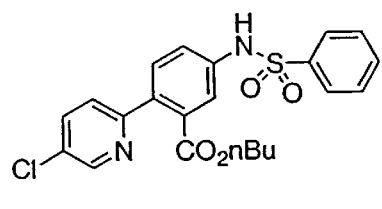
Figure 3:
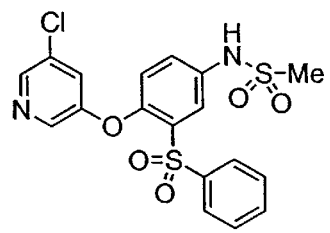
Figure 3:
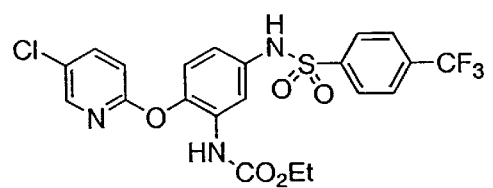
Figure 4:
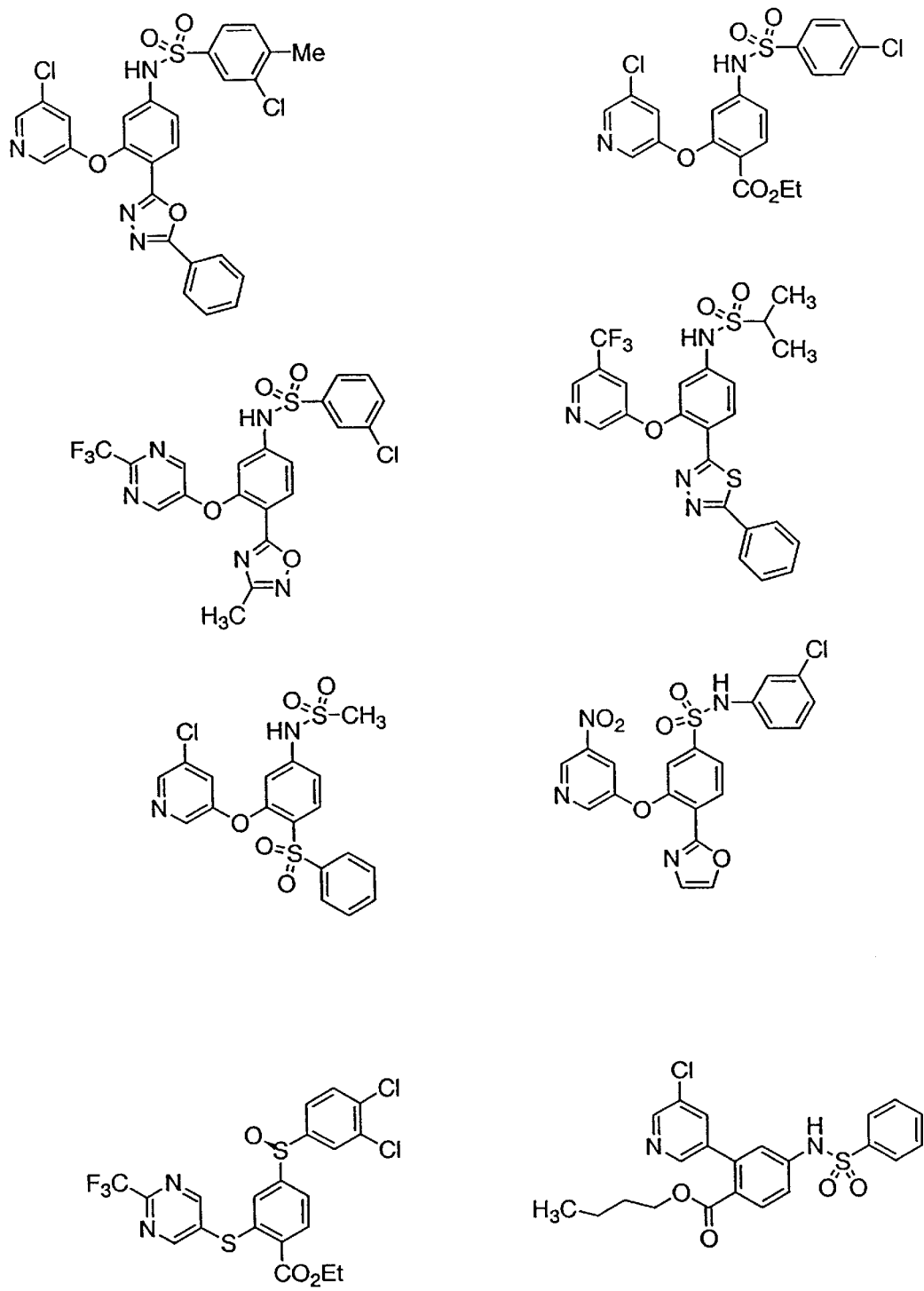

Abbreviations and Definitions:

The following abbreviations are used herein: PPARγ: peroxisome proliferator-activated receptor γ, NIDDM: noninsulin-dependent diabetes mellitus; Et₃N: triethylamine; MEOH: methanol; and DMSO: dimethylsulfoxide.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multi-valent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl,, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —CH₂CH₂CH₂CH₂—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH₂—CH₂—O—CH₃, —CH₂—CH₂—NH—CH₃, —CH₂—CH₂—N(CH₃)—CH₃, —CH₂—S—CH₂—CH₃, —CH₂—CH₂—S(O)—CH₃, —CH₂—CH₂—S(O)₂—CH₃, —CH=CH—O—CH₃, —Si(CH₃)₃, —CH₂—CH=N—OCH₃, and —CH=CH—N(CH₃)—CH₃. Up to two heteroatoms may be consecutive, such as, for example, —CH₂—NH—OCH₃ and —CH₂—O—Si(CH₃)₃. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —CH₂—CH₂—S—CH₂CH₂— and —CH₂—S—CH₂—CH₂—NH—CH₂—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom Non-limiting examples of aryl groups include phenyl, 1-naphthyl, 2-naphthyl, 4-biphenyl, l-pyrrolyl, 2-pyrrolyl, 3-pyrrolyl, 3-pyrazolyl, 2-imidazolyl, 4-imidazolyl, pyrazinyl, 2oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(l-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO₂R', —CONR'R", —OC(O)NR'R'", —NR"C(O)R', —NR'—C(O)NR"R'", NR"C(O)₂R', —NH—C(NH₂)=NH, —NR'C(NH₂)=NH, —NH—C(NH₂)=NR', —S(O)R', —S(O)₂R', —S(O)₂NR'R", —CN and —NO₂ in a number ranging from zero to (2N+1), where N is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl—($C_1$–$C_4$)alkyl groups. When R' and R" are attached to the same nitrogen atom, they can be combined with the nitrogen atom to form a 5—, 6—, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF₃ and —CH₂CF₃) and acyl (e.g., —C(O)CH₃, —C(O)CF₃, —C(O)CH₂OCH₃, and the like).

Similarly, substituents for the aryl groups are varied and are selected from: —halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R',, —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R', R" and R''' are independently selected from hydrogen, (C$_1$–C$_8$)alkyl and heteroalkyl, unsubstituted aryl, (unsubstituted aryl)—(C$_1$–C$_4$)alkyl, and (unsubstituted aryl)oxy-(C$_1$–C$_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and, salts of organic acids like glucuronic or galactunoric acids and the like (see, for example, Berge, S. M., et al, "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General:

A new class of compounds that interact with PPARγ has now been discovered. Depending on the biological environment (e.g., cell type, pathological condition of the host, etc.), these compounds can activate or block the actions of PPARγ. By activating the PPARγ receptor, the compounds will find use as therapeutic agents capable of modulating conditions mediated by the PPARγ receptor. As noted above, examples of such conditions include NIDDM. Additionally, the compounds are useful for; the prevention and treatment of complications of diabetes (e.g., neuropathy, retinopathy, glomerulosclerosis, and cardiovascular disorders), and treating hyperlipidemia. Still further, the compounds are useful for the modulation of inflammatory conditions which most recently have been found to be controlled by PPARγ (see, Ricote, et al., *Nature,* 391:79–82 (1998) and Jiang, et al., *Nature,* 391:82–86 (1998). Examples of inflammatory conditions include rheumatoid arthritis and atherosclerosis.

Compounds that act via antagonism of PPARγ are useful for treating obesity, hypertension, hyperlipidemia, hypercholesterolemia, hyperlipoproteinemia, and metabolic disorders.

EMBODIMENTS OF THE INVENTION

In one aspect, the present invention provides compounds which are represented by the formula:

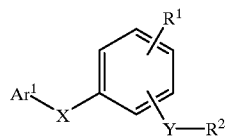

(I)

in which the symbol $Ar^1$ represents an aryl group. Preferably, $Ar^1$ is a heteroaryl group containing from 1 to 3 nitrogen atoms in the ring or rings. Particularly preferred embodiments are those in which $Ar^1$ is a monocyclic or bicyclic heteroaryl group containing from 1 to 2 nitrogen atoms in the ring or rings. Examples of such $Ar^1$ groups are 2-pyridyl, 3-pyridyl, 4-pyridyl, 2-pyrimidyl, 4-pyrimidyl, 5-pyrimidyl, 3quinolinyl, 4-isoquinolinyl, 3-pyrazolyl, 2-phenyl4-isoxazolyl and the like. More preferably, $Ar^1$ is a substituted heteroaryl group having 1 to 2 substituents selected from halogen, —$OCF_3$, —OH, —O—($C_1$–$C_6$) alkyl, —$CF_3$, ($C_1$–$C_6$)alkyl, or —$NO_2$. The most preferred embodiments are those in which $Ar^1$ is a monocyclic heteroaryl group containing 1 to 2 nitrogen atoms in the ring and being monosubstituted by halogen, —$OCF_3$ or —$CF_3$.

The letter X represents a divalent linkage selected from the group consisting of ($C_1$–$C_6$)alkylene, ($C_1$–$C_6$) alkylenoxy, —O—, —C(O)—, —$N(R^{11})$—, —$N(R^{11})C(O)$—, —$S(O)_k$— and a single bond, in which $R^{11}$ is a member selected from the group consisting of hydrogen, alkyl, heteroalkyl and arylalkyl and the subscript k is an integer of from 0 to 2. In preferred embodiments, X represents —O—, —C(O)—, a single bond, —S— or —$N(R^{11})$—, in which $R^{11}$ is hydrogen or ($C_1$–$C_6$)alkyl. More preferably, X represents —O—, —S—, —NH— or a single bond.

The letter Y, in the above formula represents a divalent linkage selected from the group consisting of alkylene, —O—, —C(O)—, —$N(R^{12})$—$S(O)_m$—, —$N(R^{12})$—$S(O)_m$—$N(R^{13})$—, —$N(R^{21})C(O)$—, —$S(O)_n$—, a single bond, and combinations thereof, in which $R^{12}$ and $R^{13}$ are members independently selected from the group consisting of hydrogen, alkyl, heteroalkyl and arylalkyl; and the subscripts m and n are independently integers of from 0 to 2. In preferred embodiments, Y represents —$N(R^{12})$—$S(O)_2$—, —$N(R^{12})$—$S(O)_2$—$N(R^{13})$—, —SO— or —$SO_2$—, in which $R^{12}$ and $R^{13}$ independently represent hydrogen or ($C_1$–$C_6$)alkyl. Most preferably, Y represents —NH—$S(O)_2$— or —NH—$S(O)_2$—NH—. Additionally, the linkages provided herein (represented by X and Y) can be in either orientation.

The symbol $R^1$ represents a member selected from the group consisting of hydrogen, alkyl, heteroalkyl, aryl, arylalkyl, arylheteroalkyl, —$CO_2R^{14}$, —$C(O)NR^{15}R^{16}$, —$C(O)R^{14}$, —$S(O)_p$—$R^{14}$, —$S(O)_q$—$NR^{15}R^{16}$, —O—C(O)—$OR^{17}$, —O—C(O)—$R^{17}$, —O—C(O)—$NR^{15}R^{16}$, —$N(R^{14})$—C(O)—$R^{17}$, —$N(R^{14})$—C(O)—$NR^{15}R^{16}$ and —$N(R^{14})$—C(O)—$OR^{17}$ in which $R^{14}$ is a member selected from the group consisting of hydrogen, alkyl, heteroalkyl, aryl and arylalkyl, and $R^{15}$ and $R^{16}$ are members independently selected from the group consisting of hydrogen, alkyl, heteroalkyl, aryl, and arylalkyl, or taken together with the nitrogen to which each is attached form a 5-, 6- or 7-membered ring. The symbol $R^{17}$ represents a member selected from the group consisting of alkyl, heteroalkyl, aryl and arylalkyl. Additionally, for the $R^1$ groups described above, the subscript p is an integer of from 0 to 3, and the subscript q is an integer of from 1 to 2. In preferred embodiments, $R^1$ represents hydrogen, ($C_1$–$C_8$)alkyl, aryl, —$CO_2R^{14}$, —$C(O)R^{14}$, —$C(O)NR^{15}R^{16}$, —$N(R^{14})$—C(O)—$R^{17}$, or —O—C(O)—$R^{17}$, in which $R^{14}$ is hydrogen, alkyl, or arylalkyl; $R^{15}$ and $R^{16}$ are independently hydrogen or alkyl, or taken together with the nitrogen to which each is attached form a 5- or 6-membered ring; and $R^{17}$ is alkyl or arylalkyl. More preferably, $R^1$ is H, —($C_1$–$C_8$)alkyl, aryl, —$C(O)R^{14}$ or —$C(O)NR^{15}R^{16}$. For those embodiments in which $R^1$ is aryl, the aryl group will preferably contain from 1 to 3 heteroatoms. The most preferred $R^1$ aryl groups are those containing 2 to 3 heteroatoms and are exemplified by the formulae:

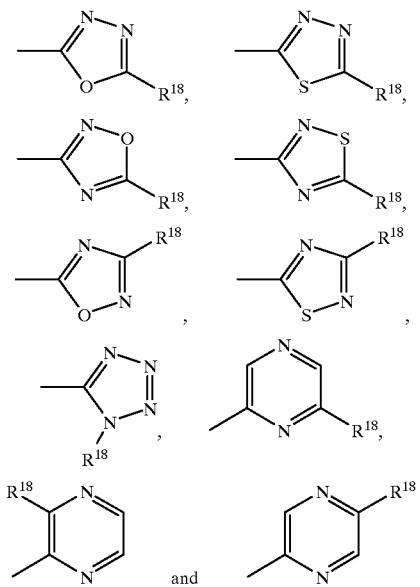

in which $R^{18}$ is selected from hydrogen, ($C_1$–$C_8$)alkyl, unsubstituted aryl, —$OR^{19}$, —$SR^{19}$ and —$NR^{20}R^{21}$, in which $R^{19}$ is H or ($C_1$–$C_8$)alkyl and $R^{20}$ and $R^{21}$ are independently selected from hydrogen and ($C_1$–$C_8$)alkyl, or taken together with the nitrogen atom to which each is attached, form a 5-, 6-, or 7-membered ring. The most preferred $R^{18}$ groups are hydrogen, ($C_1$–$C_3$)alkyl, —O—($C_{1-C3}$)alkyl, and —$NH_2$.

The symbol $R^2$ represents a member selected from the group consisting of alkyl, heteroalkyl, aryl and arylalkyl. In preferred embodiments, $R^2$ represents an aryl or arylalkyl group, more preferably an aryl group. Most preferably, $R^2$ represents a phenyl, naphthyl or pyridyl group substituted with from 1–3 substituents selected from halogen, —$OCF_3$, —OH, —O($C_1$–$C_8$)alkyl, —$CF_3$, —CN, —C(O)—($C_1$–$C_8$) alkyl, -($C_1$–$C_8$)alkyl and-$NH_2$.

In one group of particularly preferred embodiments, the compounds are represented by formula I, in which $Ar^1$ is a pyridyl ring having a single substituent selected from the group consisting of halogen, —$OCF_3$ and —$CF_3$; X is a divalent linkage selected from the group of —O—, —S—, —NH—and a single bond; Y is a divalent linkage selected from the group of —NH—$S(O)_2$— and —NH—$S(O)_2$—NH—; $R^1$ is selected from the group consisting of hydrogen, ($C_1$–$C_8$)alkyl and —$C(O)NR^{15}R^{16}$ in which $R^{15}$ and $R^{16}$ are selected from hydrogen, ($C_1$–$C_8$)alkyl, aryl and aryl($C_1$–$C_8$) alkyl; and $R^2$ is a phenyl or pyridyl ring, optionally substituted by 0–3 groups selected from halogen, ($C_1$–$C_8$)alkyl, —O—($C_1$–$C_8$)alkyl and —CN.

One of skill in the art will understand that a number of structural isomers are represented by formula I. Preferred isomers are those in which the groups on the phenyl ring occupy positions that are not contiguous. Particularly preferred compounds are those having the structural orientations represented by the formulae:

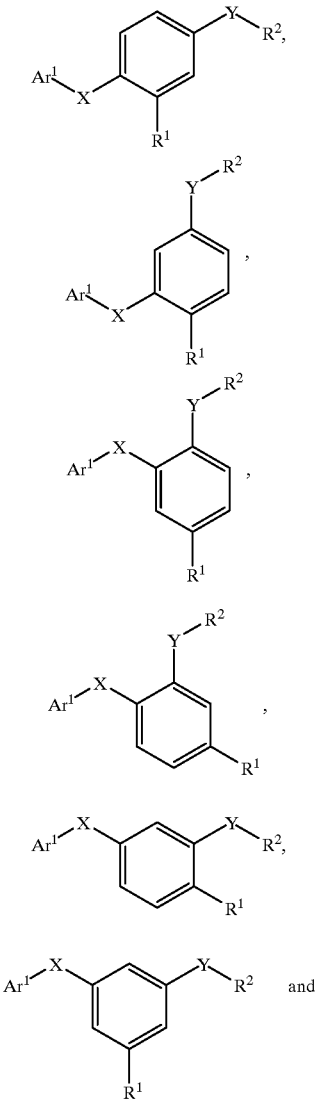

The most preferred compounds are those having the structural orientation represented by formula (Ia).

In another aspect, the present invention provides pharmaceutical compositions comprising at least one of the above compounds in admixture with a pharmaceutically acceptable excipient.

In yet another aspect, the present invention provides methods for modulating conditions mediated by PPARγ in a host. More particularly, the conditions are selected from non-insulin-dependent diabetes mellitus, obesity, and inflammatory conditions such as, for example, rheumatoid arthritis and atherosclerosis.

In still another aspect, the present invention provides methods for modulating conditions mediated by PPARγ in a host, by administering to the host a PPARγ -mediating amount of benzbromarone.

Preparation of the Compounds

The compounds of the present invention can be prepared using standard synthetic methods. For exemplary purposes, Schemes 1–5 illustrate methods for the preparation of compounds of structural formula (Ia). One of skill in the art will understand that similar methods can be used for the synthesis of compounds in the other structural classes.

As shown in Scheme 1, compounds of the present invention can be prepared beginning with the ethyl ester of commercially available 2-chloro-5-nitrobenzoic acid (i). Treatment of i with a phenol, thiophenol, or optionally protected aniline in the presence of base and heat provides the adduct (ii). Reduction of the nitro group in ii with either $H_2$ and a Pd/C catalyst or Fe/HCl provides an aniline derivative (iii). Sulfonylation of iii with an appropriate arylsulfonyl halide ($Ar'SO_2Cl$) in the presence of base (typically a tertiary amine) provides a target compound (iv). Compound iv can also be converted to a related compound of formula (v) in which the carboxylic ester is replaced with a 2-amino-1,3,4-oxadiazole ring, by treatment with semicarbazide.

Scheme 1

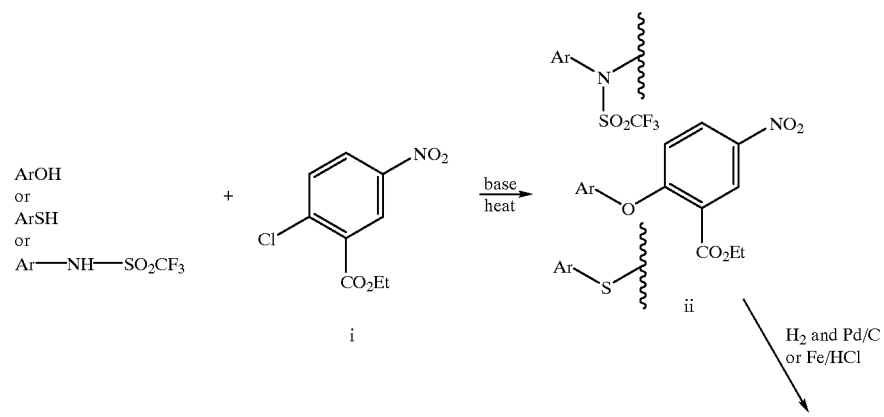

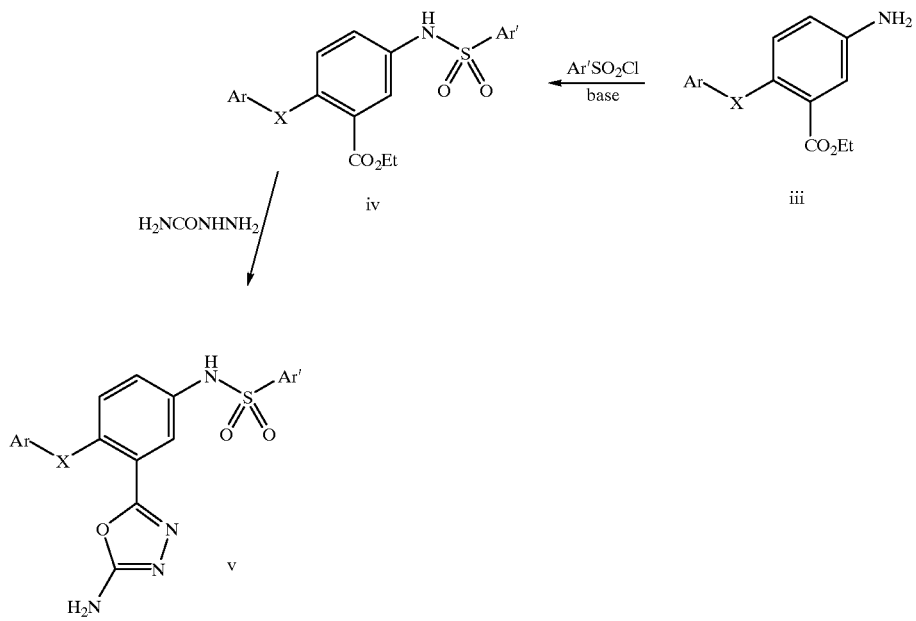

Other compounds of the present invention can be prepared beginning with i (and related compounds) as shown in Scheme 2. Treatment of i with an aryl lithium compound or aryl magnesium halide (prepared from the corresponding aryl halides) in the presence of a copper catalyst (CuCN or CuCl) provides a biaryl adduct (vi). Alternatively, biaryl adducts such as vi can be prepared directly from an aryl halide (Ar'—Cl or Ar'—Br) and i using the known Heck reaction (in the presence of palladium). Conversion of vi to suitable targets follows steps similar to those outlined in Scheme 1. As shown, the nitro group in vi can be reduced using either $H_2$ and a Pd/C catalyst or Fe/HCl to provide an aniline derivative (vii). Sulfonylation of vii with an appropriate arylsulfonyl halide (Ar"$SO_2$Cl) in the presence of base (typically a tertiary amine) provides a target compound (viii). Compound viii can also be converted to a different target compound (ix), as described above, by treatment with semicarbazide.

Scheme 2

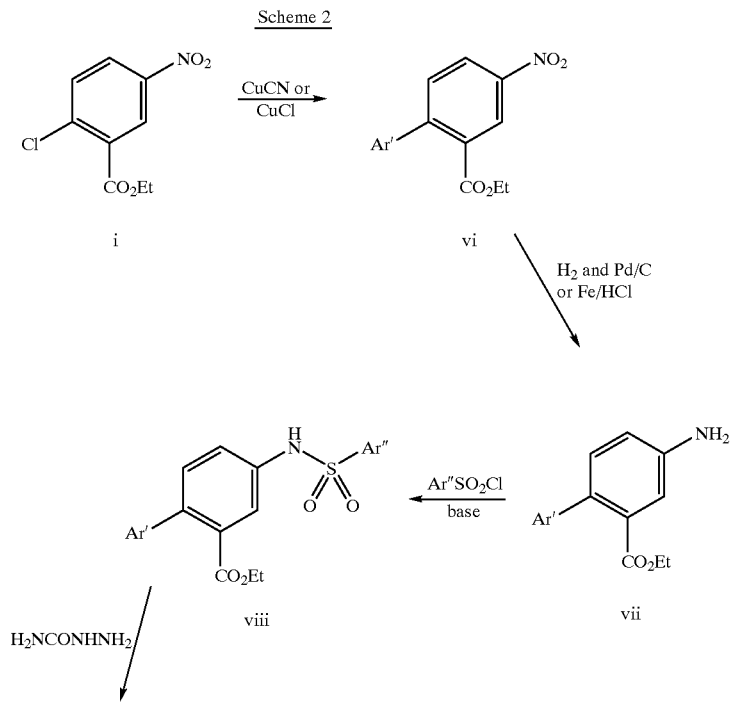

-continued

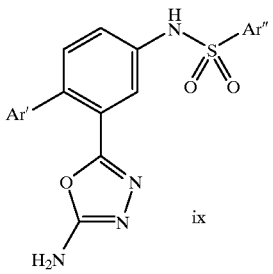

ix

Preparation of compounds of formula Ia, in which the orientation of a sulfonamide linkage is reversed, is shown in Scheme 3. Briefly, benzenesulfonic acid x (prepared by sulfonylation of commercially available ethyl 2-chlorobenzoate) can be treated with a phenol, thiophenol, or protected aniline in the presence of base and heat to provide the adducts xi, xii and xiii. Conversion of any of the adducts xi-xiii to the sulfonyl chloride (xiv) is accomplished using standard reagents (e.g., thionyl chloride, $POCl_3$, and the like). Treatment of sulfonyl chloride (xiv) with a substituted amine provides the sulfonamide (xv). Alternatively, sulfonyl chloride (xiv) can be converted to a sulfone (xvi) upon treatment with a suitable Grignard reagent (R—MgBr) or an alkyl or aryl lithium reagent (R—Li).

Scheme 3

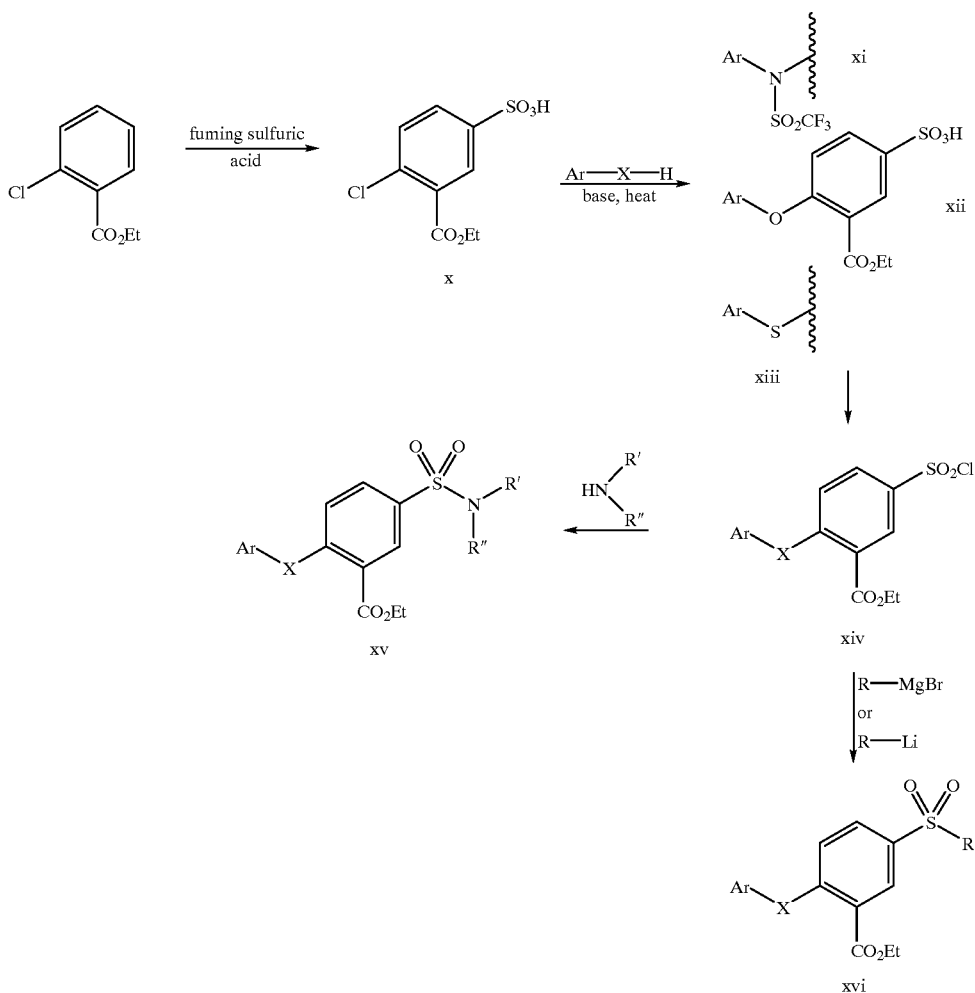

Alteration of $R^1$ groups can be accomplished using a variety of methods. Scheme 4 illustrates one method for the conversion of an ester group to a carbamate group during the construction of the target compound. One of skill in the art will understand that other chemical procedures can be employed to prepare related compounds of the invention.

Saponification of ii produces a carboxylic acid which can be converted to amine (xvii) via a Curtius rearrangement. Treatment of xvii with ethyl chloroformate in the presence of base (typically a tertiary amine) produces the carbamate (xviii). Subsequent reduction of the nitro group in xviii can be accomplished using methods outlined above to provide xix. Conversion of xix to the sulfonamide target (xx), is similarly accomplished using methods already noted.

ide followed by methylmagnesium bromide, provides ketone xxi. Baeyer-Villegar oxidation (using metachloroperbenzoic acid) produces ester xxii. Reduction of the nitro group in xxii using either $H_2$ and a Pd/C catalyst or Fe/HCl provides an aniline derivative (xiii). Sulfonylation of xxiii with an arylsulfonyl halide (Ar'$SO_2$Cl) in the presence of base (as an acid scavenger) provides a target compound (xxiv). Additional compounds of the invention can be pre-

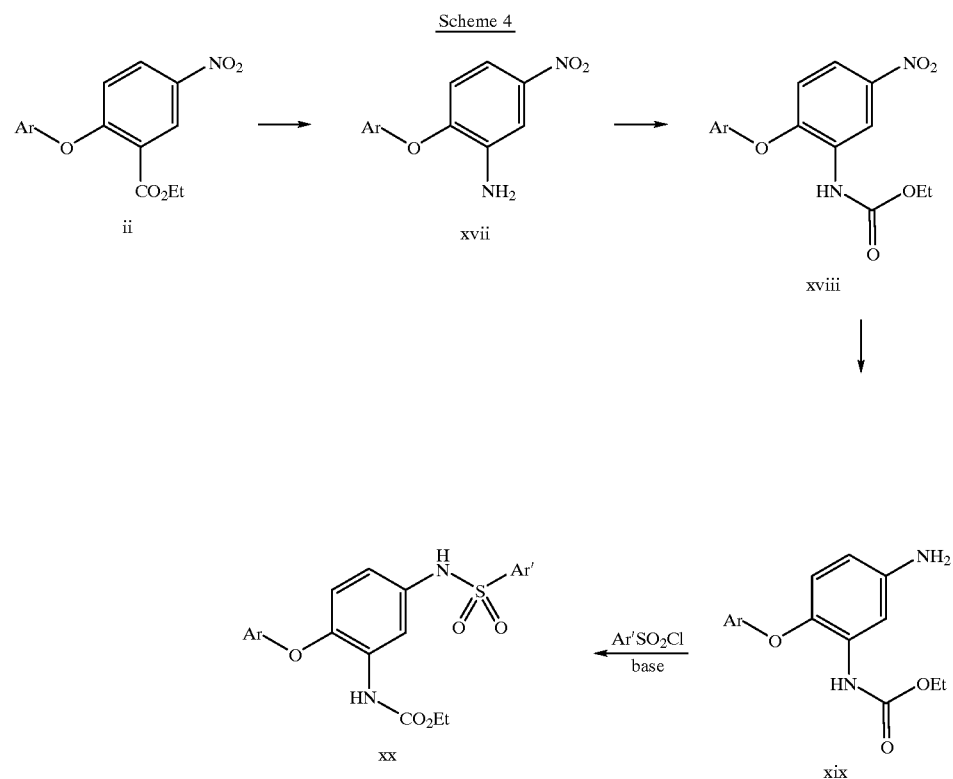

Scheme 4

Still other compounds of the invention can be prepared from ii, as outlined in Scheme 5. Thus, treatment of ii with either methyllithium (1.0 equivalents) or potassium hydroxpared by cleaving the acetate group in xxiv, and reacting the resultant hydroxy group with reagents such as methyl isocyanate to produce xxv.

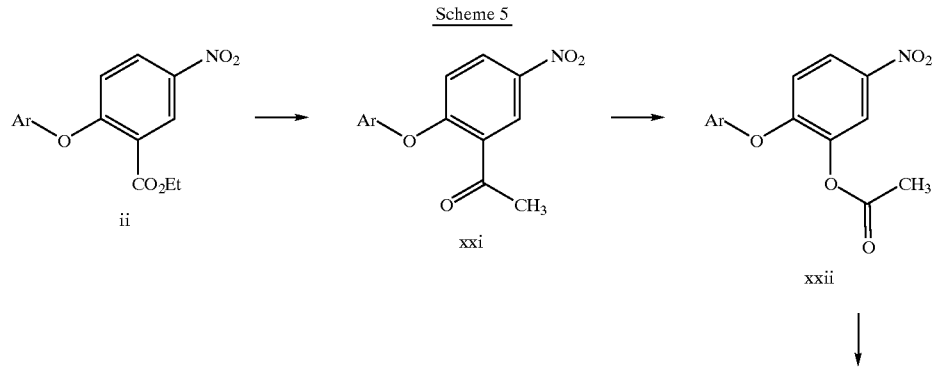

Scheme 5

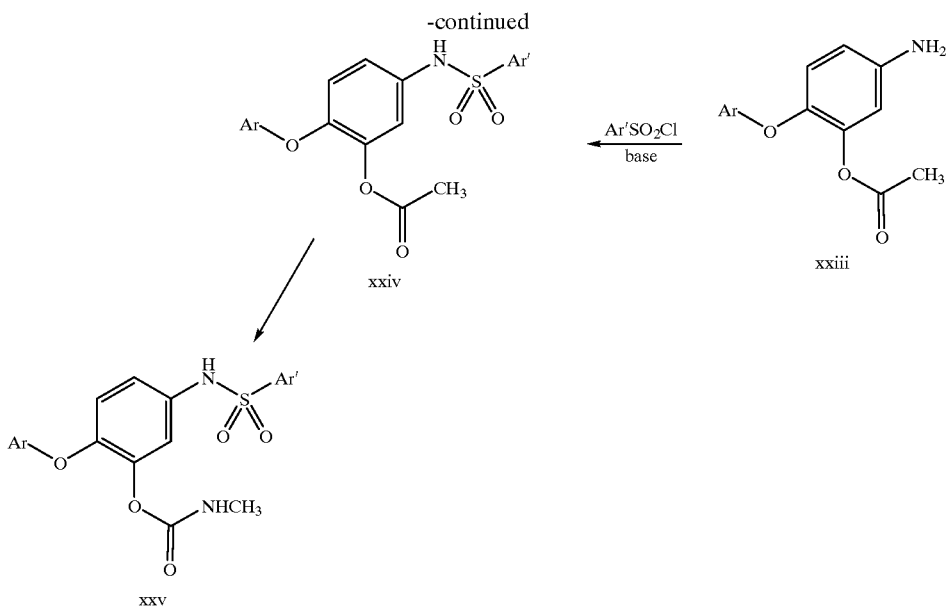

Analysis of the Compounds

The compounds of the present invention can be evaluated for modulation of the PPARγ receptor using assays such as those described in Jiang, et al., *Nature* 391:82–86 (1998), Ricote, et al., *Nature* 391:79-82 (1998) and Lehmann, et al., *J. Biol. Chem.* 270(12): 12953–12956 (1995). Alternatively, the compounds can be evaluated for their ability to displace radiolabeled BRL 49653 from a PPARγ -GST fusion protein as follows:

Materials:

PPARγ -GST fusion protein (prepared according to standard procedures), [$^3$H]—BRL 49653 having 50 Ci/mmol specific activity, Polyfiltronics Unifilter 350 filtration plate and glutathione-Sepharose® beads (from Pharmacia: washed twice with 10x binding buffer in which BSA and DTT can be left out).

Method:

Binding buffer (10 mM Tris-HCl, pH 8.0, 50 mM KCl, 10 mM DTT, 0.02% BSA and 0.01% NP-40) is added in 80 microliter amounts to the wells of the filtration plate. The test compound is then added in 10 microliters of DMSO. The PPARγ -GST fusion protein and radiolabeled BRL compound are premixed in binding buffer containing 10 mM DTT and added in 10 microliter amounts to the wells of the plate to provide final concentrations of 1 μg/well of PPARγ -GST fusion protein and 10 nM [$^3$H]-BRL 49653 compound. The plate is incubated for 15 minutes. Glutathione-agarose bead is added in 50 μL of binding buffer, and the plate is vigorously shaken for one hour. The plate is washed four times with 200 μL/well of binding buffer (without BSA and DTT). The bottom of the plate is sealed and 200 μL/well of scintillation cocktail is added. The top of the plate is then sealed and the radioactivity is determined.

Formulation and Administration of the Compounds (Compositions)

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of formula (I) or a pharmaceutically acceptable salt of a compound of formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component In tablets, the active component is mixed with the carrier having the necessary binding properties in suitable, proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment of obesity, NIDDM, or inflammatory conditions, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the[1] compound. 1 hereafter, the dosage is increased by small increments until the optimum effect under circumstances is reached. For convenience, the total daily dosage may be divided and administered in portions during the day, if desired.

The following examples are offered by way of illustration and are not intended to limit the scope of the invention.

EXAMPLES

Reagents and solvents used below can be obtained from commercial sources such as Aldrich Chemical Co. (Milwaukee, Wis., USA). [1]H—NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M—H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1100 HPLC for sample delivery. Normally the analyte was dissolved in methanol at 0.1mg/mL and 1 microliter was infused with the delivery solvent into the mass spectrometer which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2mM $NH_4OAc$ in acetonitrile/water as delivery solvent.

Example 1

This example illustrates the preparation of ethyl 5-amino-2-(3-chloro-5-pyridyloxy)benzoate.

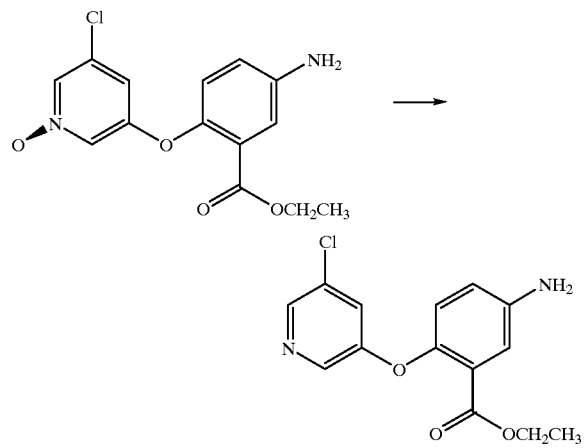

To a stirred solution of the pyridine-oxide (262 mg, 0.849 nimol, available from Maybridge Chemical Company, Cornwall, UK) in MeOH (5 mL) was added Raney nickel (1 g, 8.5 mmol, 50% slurry in water) dropwise. After 2 hr, the mixture was filtered through Celite® and the solution was evaporated to give 169 mg of the title compound as an oil, which was used without further purification.

$^1$H NMR (400 MHz) ($CD_3OD$) δ 1.13 (3H, t); 4.16 (2H, q); 6.98 (2H, s); 7.21 (1H, s); 7.29 (1H, s); 8.09 (1H, s); 8.19 (1H, s).

Example 2

This example illustrates the preparation of ethyl 5-amino-2-(3-pyridyloxy)benzoate.

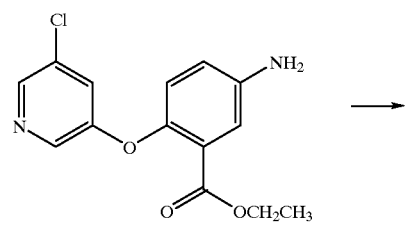

-continued

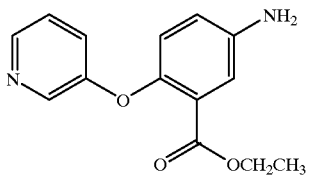

To a stirred solution of the product from Example 1 (101 mg, 0.344 mmol) in MeOH (4 mL) was added a catalytic amount of palladium on carbon. The flask was evacuated of air and placed under a balloon of hydrogen gas. After 1 hr, the mixture was filtered through Celite® and the filtrate was evaporated to provide 85 mg of the title compound (96%).

$^1$H NMR (400 MHz) (CD$_3$OD) δ 1.16 (3H, m); 4.19 (2H, m); 7.17 (2H, m); 7.52 (1H, d); 7.79 (2H, br s); 8.41 (2H, br d).

Example 3

This example illustrates the synthesis of ethyl 5-(2-methoxy-5-bromobenzenesulfonamido)-2-(3-chloro-5-pyridyloxy)benzoate.

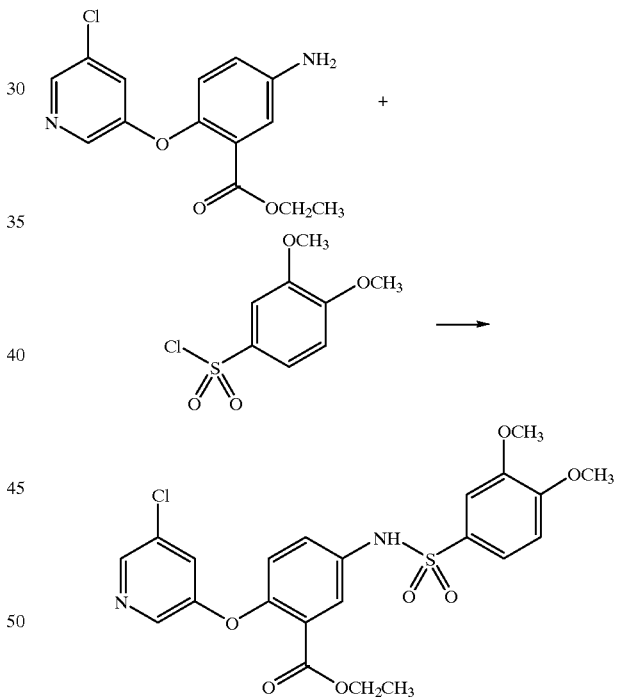

To a solution of the aniline produced in Example 1 (250 mg, 0.85 mmol) in CH$_2$Cl$_2$ (4 mL) was added 5-bromo-2-methoxybenzenesulfonyl chloride (244 mg, 0.85 mmol). The mixture was stirred for 10 hr. The title compound (94 mg, 20%) was isolated following column chromatography on silica gel (1:1 hexane/ethyl acetate).

$^1$H NMR (400 MHz) (CD$_3$OD) δ 8.20 (1H, d, J=2 Hz), 8.03 (1H, d, J=2 Hz), 7.89 (1H, d, J=3 Hz), 7.70 (1H, d, J=3 Hz), 7.65 (1H, dd, J=9, 3 Hz), 7.41 (1H, dd, J=9,3 Hz), 7.15 (1H, d, J=2 Hz), 7.08 (2H, dd, J=9,3 Hz), 4.16 (2H, q, J=7 Hz), 3.95 (3H, s), 1.26 (3H, t, J =7 Hz).

Alternatively, poly(4vinylpyridine) (250 mg, 60 mesh) can be washed with dichloromethane (2×7 mL) and diluted into dichloromethane (2 mL). The aniline produced in Example 1 (29.2 mg, 0.1 mmol) can be added followed by 5-bromo-2-methoxybenzenesulfonyl chloride (59 mg, 0.25 mmol). The reaction vessel is then agitated for ten hours and ArgoPore-NH2 (0.50 g, 1.11 mmol/gram loading) is added along with dichloromethane (6 mL). The reaction vessel is agitated for three hours and the solvent is collected. The resin is washed with dichloromethane (2×6 mL) and the dichloromethane is combined and evaporated to yield the title compound.

Example 4

This example illustrates the synthesis of ethyl 5-(3,4-dimethoxy-benzenesulfonamido)-2-(3-chloro-5-pyridyloxy)benzoate.

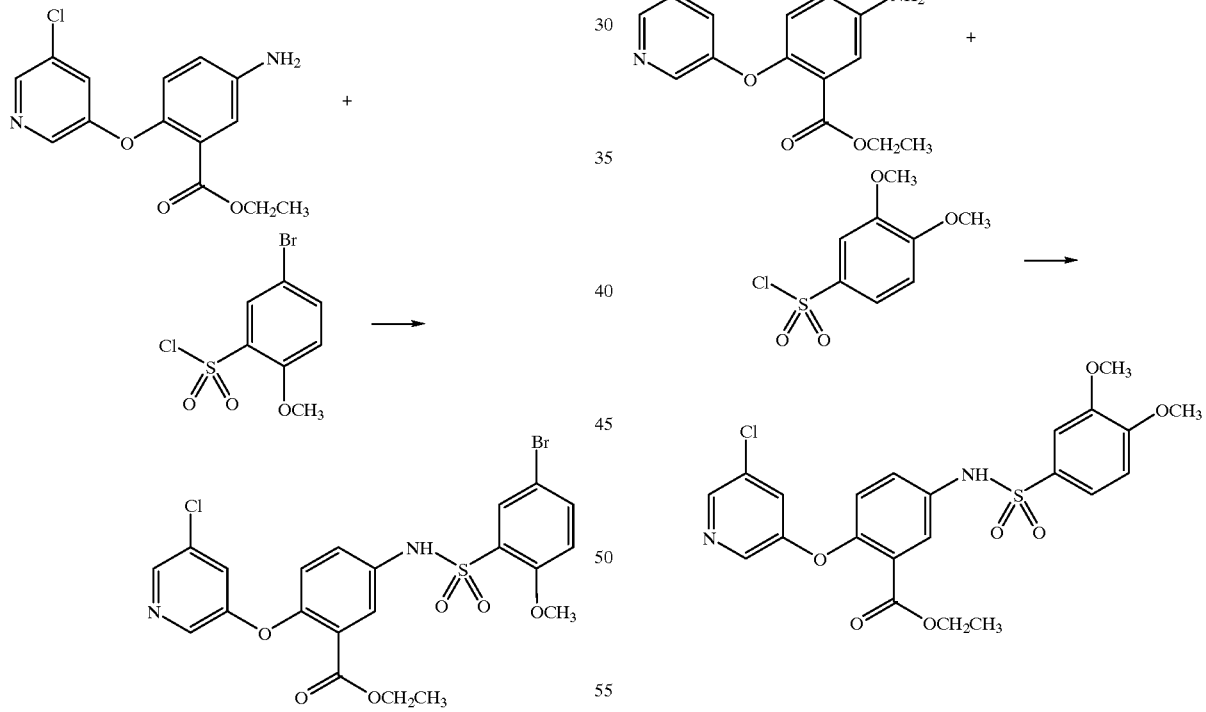

The title compound was prepared in a manner similar to Example 3, beginning with 0.1 g of the aniline of Example 1 and 3,4-dimethoxybenzenesulfonyl chloride, and adding 0.2 mL of pyridine to the reaction mixture to yield 0.115 g (68%) of the title sulfonamide.

$^1$H NMR (400 MHz) (CD$_3$OD) δ 8.22 (d, 1H, J=2 Hz), 8.05 (d, 1H, J=2 Hz), 7.68 (d, 1H, J=3 Hz), 7.38 (m, 2H), 7.27 (d, 1H, J=2 Hz), 7.20 (d, 1H,J=2 Hz), 7.10 (d, 1H, J=8 Hz), 7.01 (d, 1H, J=8 Hz), 4;16 (q, 2H, J=7 Hz), 3.85(s,3H), 3.81 (s, 3H), 1.11 (t, J=7 Hz).

Example 5

This example illustrates the synthesis of ethyl 5-(2-methyl-5-nitrobenzenesulfonamido)-2-(3-chloro-5-pyridyloxy)benzoate.

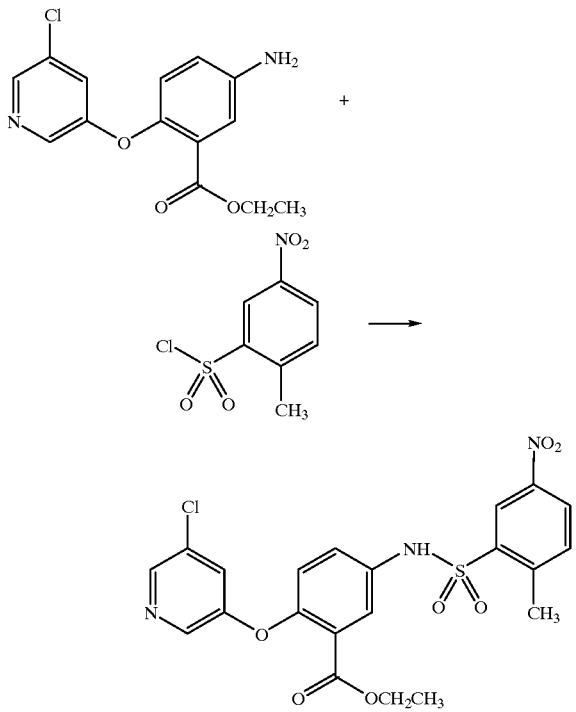

The title compound was prepared using the procedure described in Example 3, beginning with 0.1 g of the aniline of Example 1 and 2-methyl-5-nitrobenzenesulfonyl chloride and adding poly(4-vinylpyridine) (250 mg, 60 mesh) to the reaction mixture. After workup, 0.15 g (89%) of the title sulfonamide was obtained.

$^1$H NMR (400 MHz) (CD$_3$OD) δ 8.72 (d, 1H, J=2 Hz), 8.32 (d, 1H, J=8 Hz), 8.20 (d, 1H, J=2 Hz), 8.04 (d, 1H, J=2 Hz), 7.68 (d, 1H, J=2 Hz), 7.63 (d, 1H, J=8 Hz), 7.38 (d, 1H, J=8 Hz), 7.17 (d, 1H, J=2 Hz), 7.12 (d, 1H, J=8 Hz), 4.15 (q, 2H, J=7 Hz), 2.76 (s, 3H), 1.11 (t, J=7 Hz).

Example 6

This example illustrates the preparation of ethyl 5-(2,6-dichlorobenzenesulfonamido)-2-(3-chloro-5-pyridyloxy)benzoate.

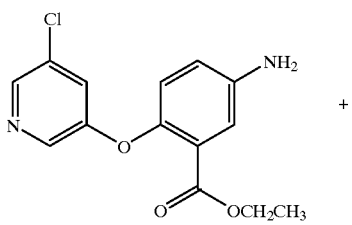

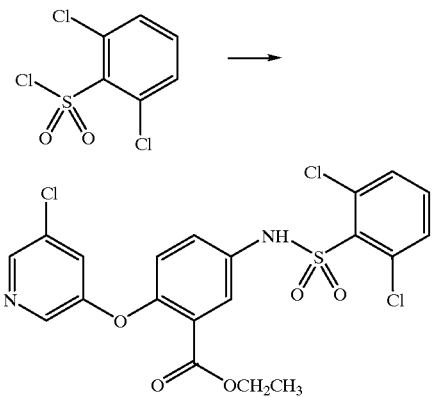

The title compound was prepared using the procedure described in Example 3, beginning with 0.1 g of the aniline of Example 1 and 2,6-dichlorobenzenesulfonyl chloride and using dimethylformamide as solvent in place of CH$_2$Cl$_2$. After workup, 0.024 g (14%) of the title sulfonamide was obtained.

$^1$H NMR (400 MHz) (CD$_3$OD) δ 8.21 (d, 1H, J=2 Hz), 8.02 (d, 1H, J=8 Hz), 7.76 (d, 1H, J=2 Hz), 7.40–7.58 (m, 4H), 7.17 (d, 1H, J=2 Hz), 7.10 (d, 1H, J=8 Hz), 4.16 (q, 2H, J=7 Hz), 1.13 (t, J=7 Hz).

Example 7

This example illustrates the preparation of ethyl 5-(2,4-dichloro-6-methylbenzenesulfonamido)-2-(3-chloro-5-pyridyloxy)benzoate.

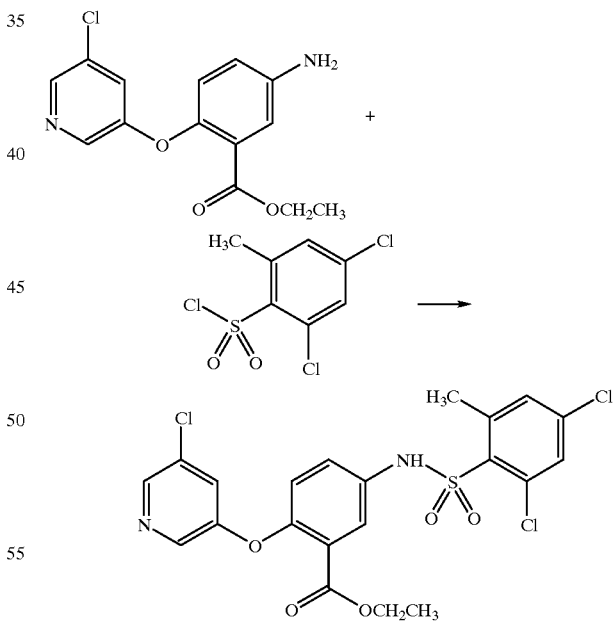

The title compound was prepared using the alternative procedure described in Example 3. In this manner, 0.1 g of the aniline of Example 1 was combined with 2,4-dichloro-6-methylbenzenesulfonyl chloride and polyvinyl pyridine to provide 0.162 g (92%) of the title sulfonamide after chromatography.

$^1$HMR (400 MHz) (CD$_3$OD) δ 8.21 (d, 1H, J=2 Hz), 8.04 (d, 1H, J=2 Hz), 7.72 (d, 1H, J=2 Hz), 7.50 (s, 1H), 7.31–7.38 (m, 2H), 7.17 (s, 1H), 7.10 (d, 1H, J=9 Hz), 4.17 (q, 2H, J=7 Hz), 2.67 (s, 3H), 1.12 (t, J=7 Hz).

Example 8

This example illustrates the preparation of ethyl 5-(4-chlorobenzenesulfonamido)-2-(3-chloro-5-pyridyloxy)benzoate

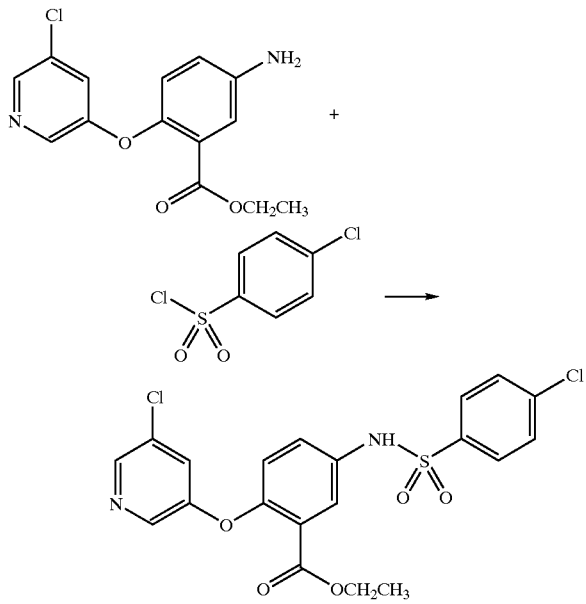

To a stirred solution of the aniline produced in Example 1 (168 mg, 0.574 mmol) in $CH_2Cl_2$ (3 mL) was added 4-chlorobenzeniesulfonyl chloride (157 mg, 0.746 mmol, commercially available from Aldrich) at once. After 20 minutes, an additional amount (48 mg, 0.230 mmol) of 4-chlorobenzenesulfonyl chloride was added and the solution was stirred overnight. The product was isolated following column chromatography (1:1 hexane/diethyl ether). Yield: 160 mg (60%).

$^1$H NMR (400 MHz) ($CD_3OD$) δ 1.14 (3H, t); 4.19 (2H, q); 6.98 (2H, s); 7.13 (1H, d); 7.24 (1H, d); 7.42 (1H, m); 7.57 (2H, d); 7.69 (1H, d); 7.79 (2H, d); 8.09 (1H, s); 8.25 (1H, s).

Example 9

This example illustrates the preparation of ethyl 5-(4-chlorobenzenesulfonamido)-2-(3-pyridyloxy)benzoate

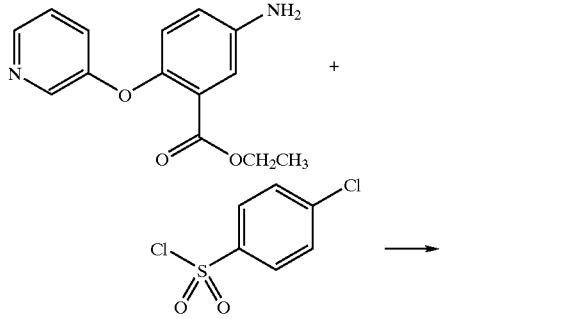

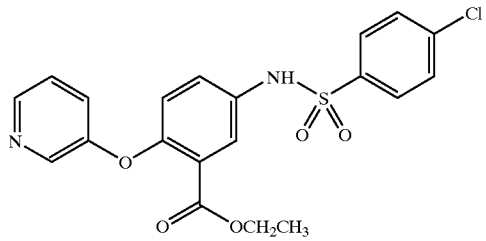

To a stirred solution of the aniline produced in Example 2 (82 mg, 0.32 mmol) in MeOH (3 mL) and THF (1 mL) was added 4-chlorobenzenesulfonyl chloride (74 mg, 0.35 mmol) followed by $Et_3N$ (89 μL, 0.64 mmol). After 20 minutes an additional amount of MeOH (1 mL) was added to aid in dissolving the reagents and the reaction mixture was allowed to stir overnight. At this time, the solvent was removed and the residue was dissolved into $CH_2Cl_2$. The resulting solution was washed three times with water and once with brine. The organic layer was evaporated and the resulting residue was purified by chromatography (1:1 hexane/diethyl ether) to provide 43.6 mg of the title compound (32% yield).

$^1$H NMR (400 MHz) ($CD_3OD$) δ 1.14 (3H, t); 4.19 (2H, q); 7.19 (1H, d); 7.24 (1H, m); 7.38 (2H, m); 7.57 (2H, d); 7.65 (1H, d); 7.79 (2H, d); 8.15 (1H, s); 8.25 (1H, s).

Example 10

This example illustrates the preparation of 5-(4-chlorobenzenesulfonamido)-2-(3-chloro-5-pyridyloxy)benzoic acid.

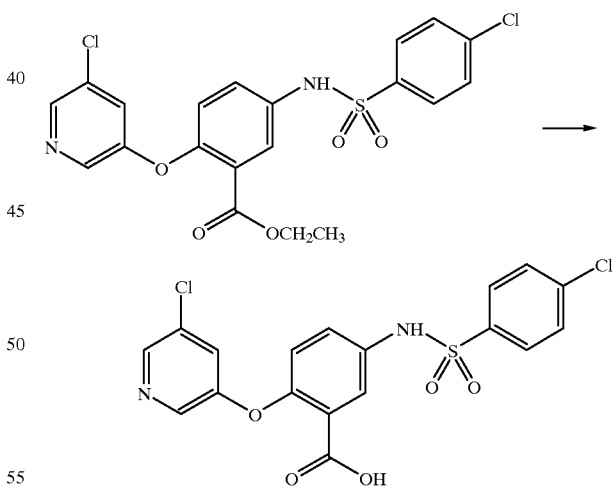

To a stirred solution of the product of Example 8 (81 mg, 0.170 mmol) in MeOH (3 mL) and water (1.0 mL) was added LiOH (89.6 mg, 3.74 mmol). The solution was stirred overnight and the solvent was evaporated to yield a white solid which was recrystallized from chloroform/ethanol. Isolated yield of the title compound: 46.5 mg, 61%.

$^1$H NMR (400 MHz) (DMSO-$D_6$) δ 7.18 (1H, d); 7.33 (1H, d); 7.35 (1H, m); 7.62 (1H, d); 7.66 (2H, d); 7.77 (2H, d); 8.16 (1H, d); 8.33 (1H, s); 10.60 (1H, s).

Example 11

This example illustrates the preparation of 5-(4-chlorobenzenesulfonamido)-2-(3-chloro-5-pyridyloxy)benzamide.

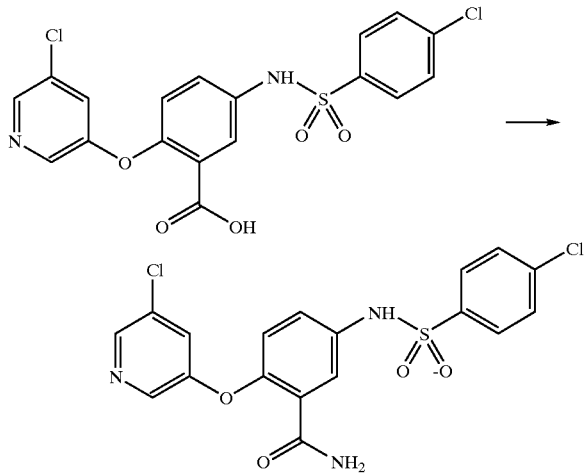

To a stirred solution of the acid from Example 10 (20 mg, 0.046 mmol) in CH$_2$Cl$_2$ (0.5 mL) and pyridine (0.5 mL) was added thionyl chloride (17 mL, 0. 228 mmol). After one hour, the solution was evaporated and placed under vacuum overnight. The residue was then dissolved in MeOH (1 mL) and CH$_2$Cl$_2$ (1 mL) and NH$_3$ (0.12 mL, 0.227 mmol, 0.757 M solution in ethanol) was added dropwise. The mixture was stirred for 8 hours and the solvent was evaporated. The residue was purified by chromatography (1:1 hexane/diethyl ether) to yield 7.3 mg of the title compound (37%).

$^1$H NMR (400 MHz) (CDCl$_3$) 6.67 (1H, d); 7.10 (1H, d); 7.23 (5H, m, 1H exch); 7.52 (2H, d); 7.89 (2H, d); 8.21 (1H, s exch); 8.45 (1H, exch).

Example 12

This example illustrates the preparation of ethyl 5-(2,4-dichloro-5-methylbenzenesulfonamido)-2-(3-chloro-5-pyridyloxy)benzoate.

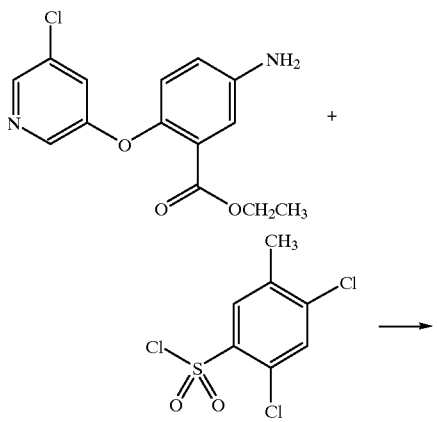

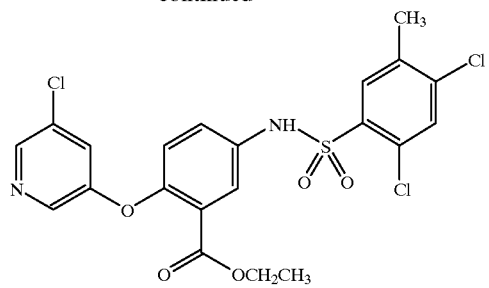

The title compound can be prepared in a manner similar to Example 3, beginning with 2,4dichloro-5-methylbenzenesulfonyl chloride, or can be purchased from Maybridge Chemical Co.

$^1$H NMR (400 MHz) (CD$_3$OD) δ 1.13 (3H, t); 2.39 (3H, s); 4.18 (2H, q); 7.10 (1H, d); 7.19 (1H, d); 7.42 (1H, dd); 7.64 (1H, s); 7.72 (1H, d); 8.01 (1H, s); 8.06 (1H, d); 8.22 (1H, d).

Example 13

This example illustrates the synthesis of 2(5-chloro-3-pyridyloxy)-5-(2,4-dichloro-5-methylbenzenesulfonamido) benzamides. Briefly, the precursor benzoic acid (0.050 g) was dissolved in dichloromethane (2 mL) and PyBroP (5 eq., 230 mg) was added followed by the amine (5 equiv.) and diisopropylethylamine1(2 equiv.). The resulting solution was stirred at room temperature for eight hr and filtered through a pad of silica gel. The product was obtained as a white solid following preparative scale HPLC.

TABLE A

| Compound | R | MS (M + H) |
|---|---|---|
| 13a | t-Bu | 542 |
| 13b | —CH$_2$CH$_2$OH | 530 |
| 13c | —NHCH$_3$ | 515 |
| 13d | —C$_6$H$_5$ | 562 |
| 13e | -2-thiazole | 569 |
| 13f | -2-furanylmethyl | 566 |
| 13g | —CH$_2$CF$_3$ | 568 |
| 13h | —CH$_2$CH(OH)CH$_2$OH | 560 |
| 13i | —N(Me) of 13b | 544 |

Example 14

This example illustrates the preparation of ethyl 5-(4-toluenesulfonamido)-2-(3-chloro-5-pyridyloxy)benzoate.

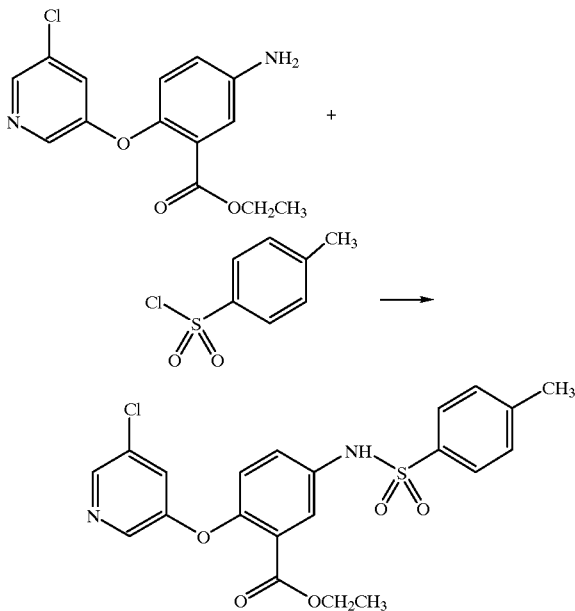

The title compound was prepared in a manner similar to Example 3, beginning with p-toluenesulfonyl chloride, or can be purchased from Maybridge Chemical Co.

$^1$H NMR (400 MHz) (CD$_3$OD) δ 1.14 (3H, t); 2.39 (3H, s); 4.17 (2H, q); 7.10 (1H, d); 7.19 (1H, d); 7.33 (2H, d); 7.40 (1H, m); 7.66–7.69 (3H, m); 8.05 (1H, d); 8.23 (1H, d); 8.25(1H, s).

Example 15

This example illustrates the preparation of 5-(4-(4-chlorobenzene-sulfonamido)phenoxy)-3-chloropyridine.

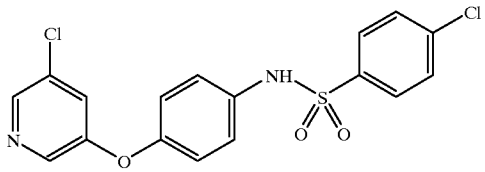

15.1 Preparation of 5(4-nitrophenoxy)-3-chloropyridine

To a stirred solution of 4-fluoro-nitrobenzene (913 μL, 8.61 mmol, from Aldrich) in dioxane (1 mL) was added 3-chloro-5-hydroxypyridine (558 mg, 4.31 mmol, from Aldrich) followed by triethylamine (661 μL, 4.74 mmol). The solution was refluxed for 4.5 hours, evaporated and the crude solid was dissolved in ethyl acetate. The solution was washed three times with saturated K$_2$CO$_3$ solution, once with, brine and then back-extracted with ethyl acetate. The two organic solutions were combined, concentrated and the residue was purified by chromatography (diethyl ether as eluant) to provide 481 mg of the title compound.

$^1$H NMR (400 MHz) (CD$_3$OD) δ 7.24 (2H, dd); 7.74 (1H, m); 8.32 (2H, dd); 8.39 (1H, m); 8.48 (1H, m).

15.2 Preparation of 5-(4-aminophenoxy)-3-chloropyridine

To a stirred solution of 5-(4-nitrophdnoxy)-3-chloropyridine (219 mg, 0.873 mmol) in EtOH (4 mL) was added SnCl$_2$ (730 mg, 3.24 mmol). The solution was refluxed for 1.25 hr and the solvent was removed by evaporation. The resulting crude solid was purified by chromatography (97.5:2.5 CH$_2$Cl$_2$:MeOH) to provide 187.7 mg (78% yield) of the title compound.

$^1$H NMR (400 MHz) (CDCl$_3$) δ 6.69 (2H, dd); 6.86 (2H, dd); 7.14 (1H, m); 8.21 (2H, m).

15.3 Preparation of 5-(4-(4-chlorobenzenesulfonamido)phenoxy)-3-chloropyridine To a stirred solution of 5-(4-aminophenoxy)-3-chloropyridine (150 mg, 60.7 mmol) in THF (2 mL) and MeOH (2 mL) was added 4-chlorosulfonylchloride (215 mg, 1.02 mmol) followed by triethylamine (142 μL, 1.02 mmol). The solution was stirred for seven hr, and concentrated. The crude solid was dissolved in methyl acetate and was washed three times with saturated K$_2$CO$_3$ solution, once with brine, and then back-extracted with ethyl acetate. The organic portions were combined, concentrated and the residue was purified by chromatography (50:50, hexane:diethyl ether as eluant) to provide 178.7 mg (51%) of the title compound.

$^1$H NMR (400 MHz) (CDCl$_3$) δ 6.97 (2H, d); 7.15 (2H,d); 7.32 (1H, m); 7.48 (2H, d); 7.72 (2H, d); 8.15 (1H, s); 8.25 (1H, s).

Example 16

The compounds in Tables B and C were prepared using methods and conditions similar to those provided in Examples 9–15, with the appropriate starting materials.

TABLE B

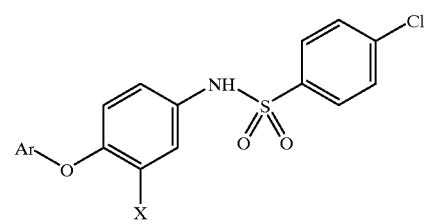

| | Ar | X | MS (M + H) |
|---|---|---|---|
| 16a (Example 10) | 5-chloro-3-pyridinyl | —CO$_2$H | 439.1 |
| 16b (Example 9) | 3-pyridinyl | —CO$_2$Et | 433 |
| 16c (Example 11) | 5-chloro-3-pyridinyl | —CONH$_2$ | 438 |
| 16d (Example 15) | 5-chloro-3-pyridinyl | —H | 395 |
| 16e | 5-chloro-3-pyridinyl | —CONH-nBu | 494 |
| 16f | 5-chloro-3-pyridinyl | —NH—CO$_2$tBu | 510 |
| 16g | 5-chloro-3-pyridinyl | —CONHMe | 452 |
| 16h | 2-methyl-3-pyridinyl | —CONHEt | |
| 16i | 2-methyl-5-pyridinyl | " | |
| 16j | 3-chlorophenyl | " | |
| 16k | 3-pyridinyl | " | |
| 16l | 5-chloro-3-pyridinyl | —CON(CH$_3$)$_2$ | 466 |
| 16m | " | —CON(CH$_2$CH$_3$)$_2$ | 494 |
| 16n | " | —CONH(3-pentyl) | 508 |
| 16o | 5-chloro-3-pyridinyl | 2-oxazolinyl | 465 |
| 16p | 5-chloro-3-pyridinyl | —CONHCH$_2$CH$_2$OH | 483 |

TABLE C

[structure: Ar—O—(phenyl with X)—NH—SO₂—(2,4-dichlorophenyl)]

| | Ar | X | mp or MS (M + H) |
|---|---|---|---|
| 16q | 5-chloro-3-pyridinyl | —CO$_2$H | 473 |
| 16r (Example 28) | 3,4-difluorophenyl | —CO$_2$Et | 106–108° C. |
| 16s (Example 27) | 3,5-difluorophenyl | —CO$_2$Et | 100–102° C. |
| 16t | 5-chloro-3-pyridinyl | —CONHCH$_2$CH$_2$OH | 516.0 |
| 16u | 5-chloro-3-pyridinyl | —CONHCH$_2$CH$_2$Cl | 533.8 |
| 16v (Example 29) | 5-chloro-3-pyridinyl | —Me | 126–128° C. |
| 16w | 3-methoxyphenyl | —CONHEt | 495 |
| 16x | 5-isoquinolinyl | —CONHEt | 516.1 |
| 16y | 6-chloro-2-pyridinyl | " | 500 |
| 16z | 5-chloro-3-pyridinyl | —SO$_2$CH$_3$ | 458 (M − H) |
| 16aa | (5-bromo-3-pyridinyl)methyl | —CONHEt | 558 |
| 16bb | 5-chloro-3-pyridinyl | —SOCH$_3$ | 491 |
| 16cc | 5-chloro-3-pyridinyl | 5-tetrazolyl | 494.9 (M − H) |
| 16dd | (5-chloro-3-pyridinyl)methyl | —CONHEt | 514.1 (M − H) |
| 16ee | 5-chloro-3-pyridinyl | —CONH—CH$_2$-(2-furanyl) | 568 |
| 16ff | " | —CONHCH$_2$CHOH—CH$_2$OH | 546 |
| 16gg | " | 5-(HOCH$_2$)-2-oxazolinyl | 528 |
| 16hh | 2-(5-ethyl-2-pyridyl)ethyl | —CONHEt | 522.2 |
| 16ii (Example 30) | 5-chloro-3-pyridinyl | —H | 132–134° C. |

Example 17

This example illustrates the preparation of N-ethyl 5-(4-iodobenzenesulfonamido)-2-(3-chloro-5-pyridyloxy)benzamide.

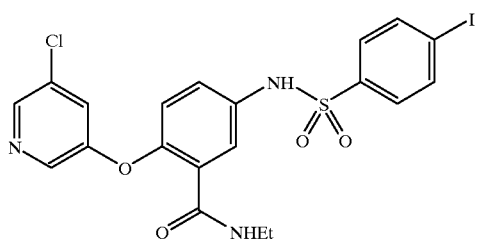

17.1 Preparation of N-ethyl-2-chloro-5-nitrobenzamide

2-Chloro-5-nitrobenzoic acid (20 g, 100 mmol) in THF (200 mL) was treated with carbonyldiimidazole (CDI) (17.8 g, 110 mmol) and triethylamine (16 mL, 110 mmol) at room temperature. After 1 hr, a solution of ethylamine (70% in water, 10 mL) was added and the mixture was stirred for 18 h. Solvent was removed by evaporation and the residue was dissolved in methylene chloride, washed with 3% KOH solution followed by water (three times) until the aqueous phase extracts were colorless. The organic phase was dried over MgSO$_4$, filtered, and the filtrate was concentrated to provide 10.4 g of N-ethyl-2-chloro-5-nitrobenzamide as light yellow crystals.

Alternatively, 2-chloro-5-nitrobenzoyl chloride (10 g, 45.5 mmol) in anhydrous dichloromethane (250 mL) with Amberlyst A-21 ion-exchange resin (17 g) was treated with a 2M THF solution of ethylamine (45 mL). The mixture was stirred at rt under nitrogen overnight. After filtration, the filtrate was concentrated to give N-ethyl-2-chloro-5-nitrobenzamide (9.0 g, 39 mmol, 86% yield) as a yellow solid.

17.2 Preparation of N-ethyl 5-nitro-2-(3-chloro-5-pyridyloxy)benzamide

To a suspension of potassium t-butoxide (1.5 g) in THF (15 mL) was added 3-chloro-5-hydroxypyridine (1.79 g, mmol). To this solution was added a solution of N-ethyl-2-chloro-5-nitrobenzamide (2.76 g, mmol) in THF (15 mL). The resulting mixture was heated at 50° C. for 84 hr. After cooling, the reaction mixture was diluted into a mixture of water and ether. Solids were collected by filtration, washed with water then with ether, and dried under vacuum to afford N-ethyl 5-nitro-2-(3-chloro-5-pyridyloxy)benzamide (2.0 g, 52%). mp 165–167° C.

$^1$H NMR (400 MHz) (DMSO-d$_6$) δ 8.544 (s, 2H); 8.476 (s, 1H); 8.436 (s, 1H); 8.303 (d, J=9 Hz, 1H); 7.860 (s, 1H); 7.247 (d, J=8.9 Hz, 1H); 3.241 (p, J=6.5 Hz, 2H); 1.047 (t, J=7.0 Hz, 3H).

17.3 Preparation of N-ethyl 5-amino-2-(3-chloro-5-pyridyloxy)benzamide

To a vigorously stirred solution of the intermediate from Example 17.2 (2.47 g) in ethanol (100 mL) and THF (20 mL) in a 500 mL round bottom flask was added a slurry of Raney Nickel (~100 mg, Aldrich). The flask was filled with H$_2$ at atmospheric pressure and the reduction was monitored by TLC. Starting material disappeared rapidly, to form a nitroso intermediate which gradually was converted to the desired aniline over about 5 hours. Stirring is stopped and as much Raney Nickel is attracted to the magnetic stirbar as possible. The solution is filtered through Celite® which was then rinsed with ethanol and methylene chloride. The combined organic portions were concentrated to provide a solid which was triturated with ether. The solid was collected and dried under vacuum to afford 2.02 g of the product aniline. mp 126–128° C.

$^1$H NMR (400 MHz) (DMSO-d$_6$) δ 8.260 (s, 1H); 8.180 (s, 1H); 8.146 (t, J=5.2 Hz, 1H); 7.230 (t, J=2.3 Hz, 1H); 6.872 (t, J=7.7 Hz, 1H); 6.749 (d, J=2.7 Hz, 1H); 6.668 (dd, J=8.6, 2.7 Hz, 1H); 3.073 (p, J=7.1 Hz, 2H); 0.881 (t, J=6.6 Hz, 3H).

17.4 Preparation of N-ethyl 5-(4-iodobenzenesulfonamido)-2-(3-chloro-5-pyridyloxy)benzamide To a suspension of N-ethyl 5-amino2-(3-chloro-5-pyridyloxy)benzamide from Example 17.3 (0.9 g) in methylene chloride (10 mL) was added 4-iodobenzenesulfonyl chloride (1.03 g), followed by pyridine (275 μL). The reaction progress was monitored by TLC, and upon completion the solvent was removed under vacuum. The resulting residue was partitioned between methylene chloride and water. The organic layer was drawn off and concentrated to form pink crystals. The crystals were dissolved in ethyl acetate (200 mL) and methanol (10 mL), and decolorized with activated charcoal. After filtration, the solution was concentrated to an oil and the residue was triturated with ether to provide 1.26 g of the title compound as colorless crystals. mp 154–156° C.

$^1$H NMR (400 MHz) (DMSO-d$_6$) δ 9.393 (s, 1H); 8.578 (br s, 1H); 8.462 (br s, 1H); 8.256 (d, J=2.2 Hz, 1H); 7.915 (d, J=7.7 Hz, 2H); 7.774 (dd, J=8.9, 1.8 Hz, 1H); 7.665 (d, J=7.7 Hz, 2H); 7.566 (t, J=5.3 Hz, 1H, NH); 7.418 (br s, 1H); 6.966 (d, J=8.8 Hz, 2H); 3.722 (p, J=6.8 Hz, 2H); 1.323 (t, J=6.6 Hz, 3H).

17.5 Preparation of N-ethyl 5-(4-iodobenzenesulfonamido)-2-(3-chloro-5-pyridyloxy)benzamide, sodium salt.

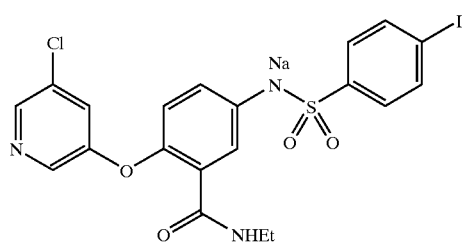

To a suspension of the compound produced in Example 17.4 (1.23 g) in methanol (15 mL) was added 1 eq of NaOH solution (2.23 mL 0.99N). Complete dissolution occurred and the solvent was removed under vacuum. The resulting oil was dissolved in 11 mL of 20% acetonitrile in water and lyophilized to afford 1.33 g of the title compound as a sodium salt monohydrate.

$^1$H NMR (400 MHz) (DMSO-d$_6$) δ 8.381 (s, 1H); 8.300 (s, 1H); 8.182 (br s, 1H); 7.867 (d, J=7.7 Hz, 2H); 7.615 (dd, J=8.9, 1.8 Hz, 1H); 7.327 (s, $^1$H); 7.055 (s, 1H); 7.038 (m, 1H); 6.877 (d, J=8.8 Hz, 1H); 3.193 (p, J=6.8 Hz, 2H); 1.006 (t, J=6.8 Hz, 3H).

$C_{20}H_{16}N_3ISO_4ClNa\cdot H_2O$ calc: %C40.18 %H 3.04 %N 7.03 found: %C 40.45% H 2.89% N 6.99

Example 18

The compounds in Table D were prepared using methods similar to those provided in Example 17, substituting the appropriate phenol, naphthol, pyridinol or quinolinol for 5-chloro-3-pyridinol, and substituting 2,4-dichloro-5-methylbenzenesulfonyl chloride for 4-iodobenzenesulfonylchloride.

TABLE D

| | Ar | MS (M + H) |
|---|---|---|
| 18a | 5-chloro-3-pyridinyl | 514 |
| 18b | 2-naphthyl | |
| 18c | 3-quinolinyl | 530 |
| 18d | 2-methyl-3-pyridinyl | 494 |
| 18e | 4-chlorophenyl | 513 |
| 18f | 3,4-difluorophenyl | 515 |
| 18g | phenyl | 479 |
| 18h | 3-chlorophenyl | 513 |
| 18i | 3-methoxyphenyl | 509 |
| 18j | 3-(N,N-dimethylamino)phenyl | 522 |

Example 19

This example illustrates the preparation of N-ethyl 5-(4-methoxybenzenesulfonamido)-2-(3-chloro-5-pyridyl oxy) benzamide

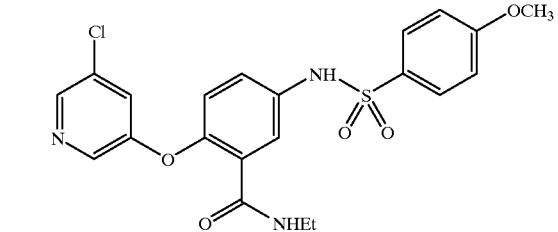

The aniline produced in Example 17.3 (0.42 g) was combined with 4-methoxybenzenesulfonyl chloride (0.297 g) under the conditions provided in Example 17.4 to provide 0.3 g of the title compound as a crystalline product after flash chromatography. mp 146–147° C.

$^1$H NMR (400 MHz) (DMSO-d$_6$) δ 10.319 (s, 1H); 8.359 (d, J=9 Hz, 1H); 8.262 (t, J=5.6 Hz, 1H); 8.213 (d, J=2.2 Hz, 1H);. 7.700 (d, J=8.4 Hz, 2H); 7.383 (t, J=2.4 Hz, 1H); 7.292 (d, J=2.4 Hz, 1H); 7.192 (dd, J=8.8, 2.4 Hz, 1H); 7.077 (d, J=8.8 Hz, 1H); 7.040 (d, J=8.8 Hz, 1H); 3.806 (s, 3H); 3.105 (p, J=7 Hz, 2H); 0.901 (t, J=7.2 Hz, 3H).

$C_{21}H_{20}N_3SO_5Cl$ calc: %C 54.60 %H 4.36 %N 9.10 found: %C 54.38 %H 4.36 %N 8.95.

Example 20

The compounds provided in Table E were prepared using the methods described in Example 17 and the appropriate aryl sulfonyl chloride.

TABLE E

[Structure: 5-chloropyridin-3-yloxy benzene with NHEt amide and sulfonamide-Y group]

| | Y | MS (M + H) |
|---|---|---|
| 20a | 4-Cl | |
| 20b | 4-NO$_2$ | |
| 20c | 2-Cl, 4-CF$_3$ | |
| 20d | 2-OCF$_3$, 4-Br | |
| 20e | 3,4-Cl$_2$ | 502 |
| 20f | 2,4-Cl$_2$, 5-CH$_3$ | 516 |
| 20g | 2,4-Cl$_2$ | 502 |
| 20h | 4-I | 559 |
| 20i | 4-tert-butyl | 489 |

Example 21

This example illustrates the preparation of ethyl 5-(5-trifluoromethyl-2-pyridinesulfonamido)-2-(3-chloro-5-pyridyloxy)benzoate.

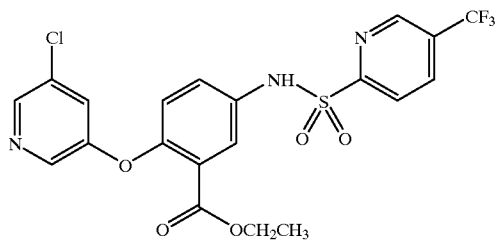

21.1 Preparation of ethyl 2-chloro-5-nitrobenzoate

A solution of 2-chloro-5-nitrobenzoic acid (26 g) in ethanol (260 mL) and concentrated sulfuric acid (1 mL) was heated at reflux for 18 hr. The reaction mixture was cooled and K$_2$CO$_3$ was added to quench the reaction. The resulting mixture was filtered and concentrated. The residue was then suspended in ether and filtered to remove insoluble starting acid. The filtrate was washed with 4% KOH (110 mL), dried over MgSO$_4$ and concentrated to provide 16.2 g of ethyl 2-chloro-5-nitrobenzoate as a colorless oil which solidified on standing.

21.2 Preparation of ethyl 5-nitro-2-(3-chloro-5-pyridyloxy)benzoate

To a solution of the ester from Example 21.1 (3 g) and 3-chloro-5-hydroxypyridine (1.79 g) in DMF (20 mL) was added 2 g of K$_2$CO$_3$. The resulting mixture was heated at 50° C. and the reaction progress was monitored by TLC. On completion, the reaction mixture was diluted into water and extracted with ether. The organic phase was dried over MgSO$_4$, filtered and concentrated to give 4.19 g of the title compound.

$^1$H NMR (400 MHz) (CDC13) δ 8.904 (d, J=2.8 Hz, 1H); 8.508 (d, J=1.9 Hz, 1H); 8.459 (dd, J=7.6, 2.8 Hz, 1H); 8.399 (d, J=2.5 Hz, 1H); 7.447 (t, J=2.3 Hz, 1H); 7.220 (d, J=9 Hz, 1H) 4.451 (q, J=7.2 Hz, 2H); 1.411 (t, J=7.2 Hz, 3H)

21.3 Preparation of ethyl 5-amino-2-(3-chloro-5-pyridyloxy)benzoate

Using the method described in Example 17.3, the product from Example 21.2 (4.1 g) in ethanol (120 mL) was converted to ethyl 5amino-2-(3-chloro-5-pyridyloxy)benzoate (1.79 g, mp 110–112° C.).

$^1$H NMR (400 MHz) (DMSO-d$_6$) δ 8.250 (s, $^1$H); 8.142 (s, $^1$H); 7.192 (s, 1H); 7.113 (s, $^1$H); 6.979 (d, J=8.4 Hz, 1H); 6.834 (d, J=8.6 Hz, 1H); 5.466 (s, 2H); 4.078 (q, J=7 Hz, 2H); 1.0091 (t, J=7 Hz, 3H)

21.4 Preparation of 5-trifluoromethyl-2-pyridinethiol

5-Trifluoromethyl-2-chloropyridine (14.75 g) was converted to 5-trifluoromethyl-2-pyridinethiol (7.12 g, mp 165–167° C.) by the method of Lansbury (J. Amer. Chem. Soc., 92: 5649 (1970)).

21.5 Preparation of 5-trifluoromethyl-2-pyridylsulfonylchloride

The pyridinethiol of Example 21.4 was converted to the corresponding sulfonyl chloride using the method of Fors, et al, J. Org. Chem. 63:7348 (1998). Briefly, the pyiridinethiol (3.5 g) was suspended in 1M HCL (53 mL) and cooled in ice. Chlorine gas was bubbled into the tared reaction flask until 3 eq (4.2 g) had been added. The resulting white solid was dissolved in cold methylene chloride (25 mL) and extracted from the HCl solution. The aqueous layer was washed with an additional 12.5 mL of methylene chloride. The presence of active chlorine was monitored by KI solution and isoprene (800 μL) was added to decompose residual chlorine. A total of 37.5 g of solution of sulfonyl chloride in methylene chloride was obtained. Rough titration of this solution with an aniline showed an effective concentration of about 0.15 g/mL. The titrated solution was kept cold (dry ice) until used.

21.6 Preparation of ethyl 5-(5-trifluoromethyl-2-pyridinesulfonamido)-2-(3-chloro-5-pyridyloxy)benzoate In a manner similar to Example 17.4, the aniline produced in Example 21.3 (0.23 g) was taken up in methylene chloride (2.5 mL) and pyridine (0.25 mL), and treated with 1.5 mL of the solution from Example 21.5. After flash chromatography and trituration with ether, the title sulfonamide (58 mg) was obtained. mp 133–135° C.

$^1$H NMR (400 MHz) (DMSO-d$_6$) δ 11.106 (s, 1H); 9.190 (dd, J=1.6, 0.8 Hz, 1H); 8.524 (dd, J=8, 2.4 Hz, 1H); 8.333 (d, J=2 Hz, 1H); 8.168 (t, J=2.8 Hz, 1H); 7.689 (d, J=2.8 Hz, 1H); 7.460 (dd, J=8.8, 3.2 Hz, 1H); 7.345 (t, J=2 Hz, 1H); 4.116 (q, J=7.2 Hz, 2H); 1.037 (t, J=7.2 Hz, 3H).

C$_{20}$H15N$_3$F$_3$SO$_5$Cl calc: %C 47.87 %H 3.01 %N 8.37 found: %C 47.93 %H 3.00 %N 8.30.

Example 22

This example illustrates the preparation of ethyl 5-(2,4-dichlorobenzene-sulfonamido)-2-(3-chloro-5-pyridyloxy)benzoate.

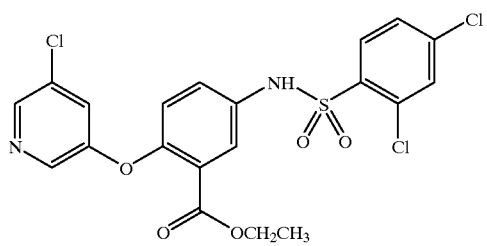

The aniline produced in Example 21.3 (1.5 g) was converted to the title compound using 2,4-dichlorobenzenesulfonyl chloride (1.26 g) in a manner similar to that described in Example 17.4. The title compound (1.99 g) was obtained as a crystalline product following flash chromatography and trituration with hexane.

$^1$H NMR (400 MHz) (CDCl$_3$) δ 8.279 (br s, 1H); 8.131 (br s, 1H); 7.966 (d, J=8.7 Hz, 1H); 7.669 (d, J=2.8 Hz, 1H); 7.560 (d, J=1.9 Hz, 1H); 7.381 (m, 2H); 7.159 (br s, 1H); 7.081 (t, J=1.9 Hz, 2H); 6.979 (d, J=8 Hz, 1H); 4.221 (q, J=7 Hz, 2H); 1.175 (t, J=7 Hz, 3H).

Example 23

The compounds provided in Table F were prepared using the methods described in Example 22 and the appropriate aryl sulfonyl chloride.

TABLE F

| | Y | MS (M + H) |
|---|---|---|
| 23a (Example 14) | 4-CH$_3$ | 447 |
| 23b (Example 3) | 2-OCH$_3$, 5-Br | 542.9 |
| 23c | 3-Cl, 4-F | |
| 23d (Example 4) | 3,4-(OCH$_3$)$_2$ | 493 |
| 23e | 3,4-Cl$_2$ | |
| 23f (Example 5) | 2-CH$_3$, 5-NO$_2$ | 492 |
| 23g (Example 6) | 2,6-Cl$_2$ | 503 |
| 23h (Example 7) | 2,4-Cl$_2$, 6-CH$_3$ | 517 |
| 23i (Example 8) | 4-Cl | 467 |

Example 24

This example illustrates the preparation of ethyl 5-(6-chloro-3-pyridinesulfonamido)-2-(3-chloro-5-pyridyloxy)benzoate.

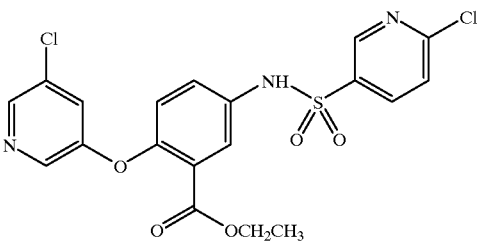

The aniline produced in Example 21.3 was converted to the title compound using 2-chloropyridine-5-sulfonyl chloride in a manner similar to that described in Example 17.4. The title compound was obtained as a crystalline product following flash chromatography and trituration with hexane. mp 166–168C.

$^1$H NMR (400 MHz) (CDCl$_3$) δ 10.827 (s, $^1$H); 8.745 (d, J=2.6 Hz, 1H); 8.341 (d, J=1.8 Hz, 1H); 8.184 (d, J=2.6 Hz, 2H); 8.152 (dd, J=8.4, 2.6 Hz, 1H); 7.762 (d, J=8.4 Hz, 1H); 7.62 (d, J=2.7 Hz, 1H); 7.397 (dd, J=8.6, 2.8 Hz, 1H); 7.381 (d, J=1.1 Hz, 1H); 7.269 (d, J=8.8 Hz, 1H); 4.121 (q, J=7 Hz, 2H); 1.043 (t, J=7.1 Hz,, 3H).

C$_{19}$H$_{15}$N$_3$Cl$_2$SO$_5$ calc: %C 48.73 %H 3.23 %N 8.97 found: %C 48.49 %H 3.33 %N 8.71.

Example 25

This example illustrates the preparation of ethyl 5-(3-pyridinesulfonamido)-2-(3-chloro-5-pyridyloxy)benzoate.

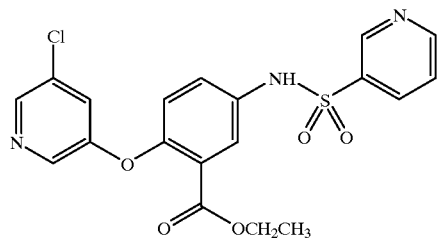

The aniline produced in Example 21.3 was converted to the title compound using pyridine-3-sulfonyl chloride in a manner similar to that described in Example 17.4. The title compound was obtained as a crystalline product following flash chromatography and trituration with ethyl acetate/hexane. mp 120–122° C., $^1$H NMR (400 MHz) (CDCl$_3$) δ 10.775 (s, 1H); 8.906 (d, J=1.8 Hz, 1H); 8.817 (d, J=1.6 Hz, 1H); 8.334 (d, J=2.1 Hz, 1H);; 8.159 (d, J=2.5 Hz, 1H); 8.138 (ddd, J=8.1, 2.4, 1.1 Hz, 1H); 7.630 (ddd, J=8.1, 4.8, 1.1 Hz, 1H); 7.623 (d, J=2.9 Hz, 1H); 7.393 (dd, J=8.8, 2.8 Hz, 1H); 7.358 (d, J=2.3 Hz, 1H); 7.228 (d, J=8.8 Hz, 1H); 4.113 (q, J=7.2 Hz, 2H); 1.035 (t, J=7.1 Hz,, 3H).

C$_{19}$H$_{16}$N$_3$ClSO$_5$ calc: %C 52.60 %H 3.72 %N 9.68 found: %C 52.54 %H 3.78 %N 9.40.

Example 26

This example illustrates the preparation of N-ethyl 5-(5-trifluoromethyl-2-pyridinesulfonamido)-2-(3-chloro-5-pyridyloxy)benzamide.

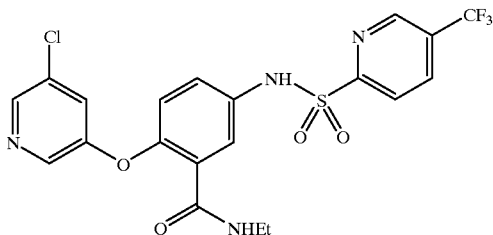

The aniline (56 mg) produced in Example 17.3 was converted to the title compound using the sulfonyl chloride produced in Example 21.5, in a manner similar to that described in Example 21.6. The title compound (33 mg) was obtained as a crystalline product. mp 147–148° C.

$^1$H NMR (400 MHz) (DMSO-d$_6$) δ 10.989 (s, 1H); 9.189 (s, $^1$H); 8.532 (d, J=8.4 Hz, 1H); 8.363 (d, J=2.4 Hz, 1H); 8.278 (t; J=5.2 Hz, 1H); 8.229 (d, J=2.4 Hz, 1H); 8.193 (d, J=8 Hz, 1H); 7.416 (d, J=2 Hz, 1i); 7.350 (d, J=2.8 Hz, 1H); 7.266 (dd, J=8.4, 2.4 Hz, 1H); 7.050 (d, J=8.8 Hz, 1H); 3.16S (p, J=6.8 Hz, 2H); 0.904 (t, J=6.8 Hz, 3H).

Example 27

This example illustrates the preparation of ethyl 5-(2,4-dichlorophenylsulfonamido)-2-(3,5-difluorophenoxy)benzoate.

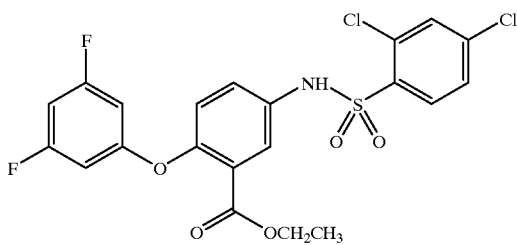

27.1 Preparation of ethyl 5-nitro-2-(3,5-difluorophenoxy)benzoate

Using the method described in Example 21.2, ethyl 2-chloro-5-nitrobenzoate (0.6 g) and 3,5-difluorophenol (0.34 g) were combined to provide 0.8 g of the title compound.

$^1$H NMR (400 MHz) (CDCl$_3$) δ 8.955 (d, J=2.9 Hz, 1H); 8.497 (dd, J=9.1, 2.8 Hz, 1H); 7.272 (d, J=9.2 Hz, 1H); 6.797 (dd, J=11, 8.8 Hz, 1H); 6.688 (dd, J=6.9, 1.4 Hz, 1H) 4.501 (q, J=7 Hz, 2H); 1.465 (t, J=7.1 Hz, 3H).

27.2 Preparation of ethyl 5-amino-2-(3,5-difluorophenoxy)benzoate

Using the method of Example 17.3, ethyl 5-nitro-2-(3,5-difluorophenoxy)benzoate (0.76 g) in ethanol (7 mL) and THF (3 mL) was converted to the corresponding aniline derivative which was obtained as an oil (0.696 g).

$^1$H NMR (400 MHz) (CDCl$_3$) δ 7.108 (d, J=2.9 Hz,, 1H); 7.097 (s, $^1$H); 6.762 (d, J=8.6 Hz, 1H); 6.692 (dd, J=8.6, 2.9 Hz, 1H); 6.263 (tt, J=9, 2.2 Hz, 1H); 6.182 (dd, J=8.7, 2.2 Hz, 1H); 4.037 (q, J=7.2 Hz, 2H); 0.988 (t, J=7.1 Hz, 3H).

27.3 Preparation of ethyl 5-(2,4-dichlorobenzenesulfonamido)-2-(3,5-difluorophenoxy)benzoate To the aniline product of Example 27.2 (0.175 g) was added 2,4-dichlorobenzenesulfonyl chloride ((0.149 g) under conditions similar to those employed in Example 17.4. The title compound was obtained as a crystalline product (0.227 g) following flash chromatography and trituration with hexane. mp 100–102° C.

$^1$H NMR (400 MHz) (CDCl$_3$) δ 7.973 (d, J=8.5 Hz, 1H); 7.664 (d, J=2.8 Hz, 1H); 7.567 (d, J=1.9 Hz, 1H); 7.381 (m, 2H); 7.174 (br s, $^1$H); 6.997 (d, J=8.8 Hz, 2H); 6.502 (tt, J=8.9, 2.3 Hz, 1H); 6.324 (m, 2H); 4.232(q, J=7.2 Hz, 2H); 1.192 (t, J=7.1 Hz, 3H).

$C_{21}$, $H_{15}F_2Cl_2SNO_5$ calc: %C 50.21 %H 3.01 %N 2.79 found: %C 50.46 %H 3.13 %N 2.82.

Example 28

This example illustrates the preparation of ethyl 5-(2,4-dichlorobenzenesulfonamido)-2-(3,4-difluorophenoxy)benzoate.

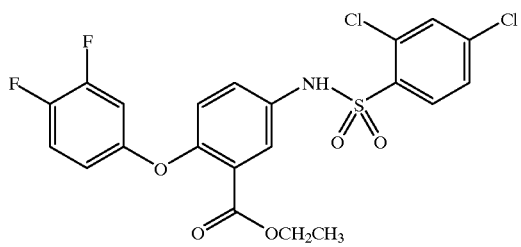

28.1 Preparation of ethyl S-nitro-2-(3,4-difluorophenoxy)benzoate

Using the method described in Example 21.2, ethyl 2-chloro-5-nitrobenzoate (0.6 g) and 3,4difluorophenol (0.34 g) were combined to provide 0.8 g of the title compound as an oil.

$^1$H NMR (400 MHz) (CDCl$_3$) δ 8.772 (d, J=2.9 Hz, 1H); 8.288 (dd, J=9.1, 2.9 Hz, 1H); 7.206 (d, J=8.9 Hz, 1H); 6.980 (d, J=9.2 Hz, 1H); 6.928 (ddd, J=10.6, 6.5, 2.9 Hz, 1H); 4.383 (q, J=7.1 Hz, 2H); 1.358 (t, J=7.1 Hz, 3H).

28.2 Preparation of ethyl 5-amino-2-(3,4-difluorophenoxy)benzoate

Using the method of Example 17.3, ethyl 5-nitro-2-(3,4-difluorophenoxy)benzoate (0.76 g) in ethanol (8 mL) was converted to the corresponding aniline derivative which was obtained as an oil (0.67 g).

$^1$H NMR (400 MHz) (CDCl$_3$) δ 7.233 (d, J=2.8 Hz, 1H); 7.018 (q, J=9 Hz, 1H); 6.877 (d, J=8.6 Hz, 1H); 6.821 (dd, J=8.6, 2,1.9 Hz, 1H); 6.646 (ddd, J=11.7, 6.6, 3 Hz, 1H); 6.542 (dtd, J=9.1, 3.2, 1.7 Hz, 1H); 4.191 (q, J=7.2 Hz, 2H); 1.150 (t, J=7.1 Hz, 3H).

28.3 Preparation of ethyl 5-(2,4-dichlorobenzenesulfonamido)-2-(3,4-difluorophenoxy)benzoate To the aniline product of Example 28.2 (0.17 g) was added 2,4-dichlorobenzenesulfonyl chloride ((0.15 g) under conditions similar to those employed in Example 17.4. The title compound was obtained as crystals (80 mg) following flash chromatography and trituration with ether. mp 106–108° C.

¹H NMR (400 MHz) (DMSO-d₆) δ 10.974 (s, 1H); 8.030 (d, J=8.5 Hz, 1H); 7.904 (d, J=1.9 Hz, 1H); 7.649 (dd, J=8,5, 2.1 Hz, 1H); 7.570 (d, J=2.7 Hz, 1H); 7.364 (d, J=9.2 Hz, 1H); 7.327 (dd, J=8,8, 2.7 Hz, 1H); 7.085 (d, J=8.9 Hz, 1H); 6.981 (ddd, J=9.7, 6.7, 3 Hz, 1H); 6.599 (dt, J=9, 1.4 Hz, 1H); 4.126 (q, J=7 Hz, 2H); 1.082 (t, J=7 Hz, 3H).

$C_{21}H_{15}NSO_5Cl_2F_2$ calc: %C 50.21 %H 3.01 %N 2.79 found: %C 50.16 %H 3.03 %N 2.81.

Example 29

This example illustrates the preparation of 4-(3-chloro-5-pyridyloxy)-5-(2,4-dichlorobenzenesulfonamido)toluene.

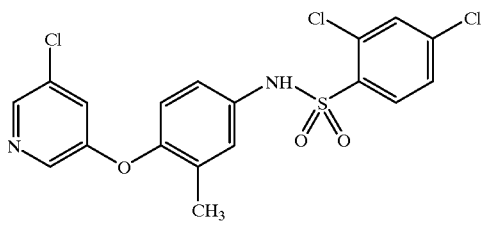

29.1 Preparation of 2-(3-chloro-5-pyridyloxy)-5-nitrotoluene

2-Fluoro-5-nitrotoluene (5.08 g) and 3-chloro-5-hydroxypyridine (4.25 g) were combined at 80° C. using a method similar to that of Example 21.2 to provide 7.1 g of 2-(3-chloro-5-pyridyloxy)-5-nitrotoluene. mp 80–82° C.

¹H NMR (400 MHz) (CDCl₃) δ 8.438 (d, J=2 Hz, 1H); 8.316 (d, J=2.3 Hz, 1H); 8.210 (d, J=2.6 Hz, 1H); 8.083 (d,d, J=8.8, 2.9 Hz, 1H); 7.337 (t, J=2.2 Hz, 1H); 6.872 (t, J=7.7 Hz, 1H); 6.913 (d, J=8.8 Hz, 11H); 2.403 (s, 3H).

29.2 Preparation of 2-(3-chloro-5-pyridyloxy)-5-aminotoluene

The nitrotoluene derivative (2.96 g) produced in Example 29.1 was converted to the corresponding amine derivative using the method described in Example 17.3 (with methanol/THF as solvent). The title compound was obtained as a solid (2.67 g). mp 48–50° C.

¹H NMR (400 MHz) (CDCl₃) δ 8.629 (m, J=2 Hz, 2H); 7.485 (t, J=2.2 Hz, 1H); 7.220 (d, J=8.4 Hz, 1H); 7.027 (d, J=2.9 Hz, 1H); 6.971 (dd, J=8.4, 2.6 Hz, 1H); 2.512 (s, 3H).

29.3 Preparation of 2-(3-chloro-5-pyridyloxy)-5-(2,4-dichlorobenzenesulfonamido)toluene To the aminotoluene product of Example 29.2 (0.42 g) was added 2,4-dichlorobenzenesulfonyl chloride ((0.444 g) under conditions similar to those employed in Example 17.4. The title compound was obtained as a crystalline product (0.473 g) following flash chromatography and trituration with hexane. mp 126–128° C.

¹H NMR (400 MHz) (CDCl₃) δ 8.284 (s, 1H); 8.145 (s, 1H); 7.951 (d, J=8.5 Hz, 1H); 7.557 (d, J=2 Hz, 1H); 7.358 (dd, J=8.5, 2 Hz, 1H); 7.127 (br s, 1H); 7.078 (m, 2H); 6.968 (dd, J=8.7, 2.6 Hz, 1H); 6.805 (d, J=8.7 Hz, 1H); 2.148 (s, 3H).

$C_{18}H_{13}N_2Cl_3SO_3$ calc: %C 48.72 %H 2.95 %N 6.31 found: %C 48.81 %H 3.03 %N 6.25.

Example 30

This example illustrates the preparation of 1-(3chloro-5-pyridyloxy)4-(2,4-dichlorobenzenesulfonamido)benzene.

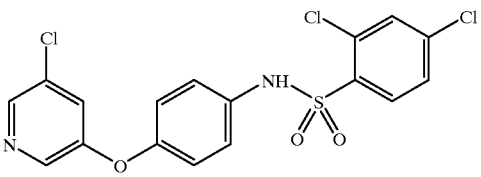

30.1 Preparation of 4-(3-chloro-5-pyridyloxy)-nitrobenzene

4-Fluoro-nitrobenzene (5.0 g) and 3chloro-5-hydroxypyridine (4.59 g) were combined at 60° C. using a method similar to that of Example 21.2 to provide 7.78 g of 4-(3-chloro-5-pyridyloxy)nitrobenzene. mp 80–82° C.

¹H NMR (400 MHz) (CDCl₃) δ 8.492 (d, J=1.9 Hz, 1H); 8.380 (d, J=2.4 Hz, 1H); 8.289 (d, J=9.2 Hz, 2H); 7.443 (d, J=2.2 Hz, 1H); 7.115 (d, J=9.2 Hz, 1H).

30.2 Preparation of 4-(3-chloro-5-pyridyloxy)-aniline

The nitrobenzene derivative (7.7 g) produced in Example 30.1 was converted to the corresponding aniline derivative using the method described in Example 17.3 (with methanol/THF as solvent). The title compound was obtained as a solid (6.7 g).

30.3 Preparation of 1-(3-chloro-5-pyridyloxy)4-(2,4-dichlorobenzenesulfonamido)benzene To the aniline product of Example 30.2 (0.45 g) was added 2,4-dichlorobenzenesulfonyl chloride ((0.533 g) under conditions similar to those employed in Example 17.4. The title compound was obtained as a crystalline product (0.643 g) following flash chromatography and trituration with ethyl acetate/hexane. mp 132–134° C.

¹H NMR (400 MHz) (CDCl₃) δ 10.709 (s, 1H); 8.388 (d, J=1.8 Hz, 1H); 8.251 (d, J=2 Hz, 1H); 7.987 (d, J=8.5 Hz, if); 7.874 (d, J=2 Hz, 1H); 7.610 (dd, J=8.7, 2 Hz, 1H); 7485 (d, J=2.1 Hz, 1H); 7.133 (d, J=9 Hz, 2H); 7.039 (d, J=9 Hz, 2H).

$C_{,17}H_{11}N_2Cl_3SO_3$ calc: %C 47.52 %H 2.58 %N 6.52 found: %C 47.69 %H 2.65 %N 6.51.

Example 31

This example illustrates the preparation of 2-(3-chloro-5-pyridyloxy)-5-(5-trifluoromethyl-2-pyridinesulfonamido)toluene.

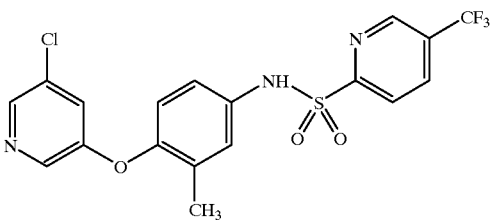

The aniline produced in Example 291.2 (0.195 g) was converted to the title compound using the sulfonyl chloride produced in Example 21.5 (1.5 mL of solution), in a manner similar to that described in Example 21.6. The title compound was obtained as a crystalline product (85 mg) after filtration of the crude product through silica and trituration in ether. mp 147–148° C.

¹H NMR (400 MHz) (CDCl₃) δ 10.795 (s, ¹H); 9.192 (br s, 1H); 8.509 (dd, J=8.2, 1.9 Hz, 1H); 8.352 (d, J=1.9 Hz, 1H); 8.1i90 (d, J=2.6 Hz, 1H); 8.171 (d, J=8.6 Hz, 1H); 7.334 (t, J=2.2 Hz, 1H); 7.128 (d, J=2.2 Hz, 1H); 7.017 (dd, J=8.6, 2.8 Hz, 1H); 6.936 (d, J=8.6 Hz, 1H); 2.082 (s, 3H).

C₁₈H₁₃N₃Cl₃SO₃•0.25H₂O calc: %C 48.22 %H 3.04 %N 9.37 found: %C 48.16 %H 2.97 %N 9.22.

Example 32

This example illustrates the preparation of 1-(3-chloro-5-pyridyloxy)-2-(2,4-dichlorobenzenesulfonamido)benzene.

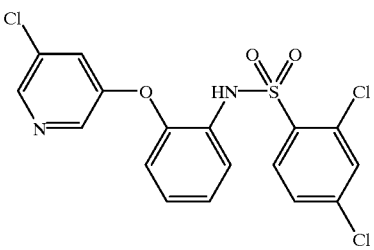

32.1 Preparation of 2-(3-chloro-5-pyridyloxy)-nitrobenzene

2-Fluoro-nitrobenzene (5.0 g) and 3,chloro-5-hydroxypyridine (4.59 g) were combined at 80° C. for 1 hr, using a method similar to that of Example 21.2 to provide 8.56 g of 2-(3-chloro-5-pyridyloxy)nitrobenzene.

32.2 Preparation of 2-(3-chloro-5-pyridyloxy)-aniline

The nitrobenzene derivative (8.56 g) produced in 32.1 was converted to the corresponding aniline derivative using the method described in Example 17.3. The title compound was obtained as a solid (4.96 g). mp 90–92° C.

32.3 Preparation of 1-(3-chloro-5-pyridyloxy)-2-(2,4-dichlorobenzenesulfonamido)benzene To the aniline product of Example 32.2 (0.41 g) was added 2,4-dichlorobenzenesulfonyl chloride ((0.452 g) under conditions similar to those employed in Example 17.4. The title compound was obtained as a crystalline product (0.278 g) following flash chromatography and trituration with methylene chloride/methanol. mp 168–170° C.

¹H NMR (400 MHz) (CDCl₃) δ 10.373 (s, 1H); 8.318 (d, J=1.9 Hz, 1H); 7.982 (d, J=2.2 Hz, 1H); 7.793 (d, J=8.6 Hz, 1H); 7.538 (d, J=2.2 Hz, 1H); 7.474 (dd, J=8.4, 2 Hz, 1H); 7.429 (dd, J=7.6, 2 Hz, 1H); 7.264 (m, 2H); 7.070 (dd, J=7.6, 2 Hz, 1H); 6.897 (t, J=2.2 Hz, 1H).

C₁₇H₁₁N₂Cl₃SO₃ calc: %C 47.52 %H 2.58 %N 6.52 found: %C 47.26 %H 2.57 %N 6.42.

Example 33

This example illustrates the preparation of 1-(3-chloro-5-pyridyloxy)-2-(4-methoxybenzenesulfonamido)benzene.

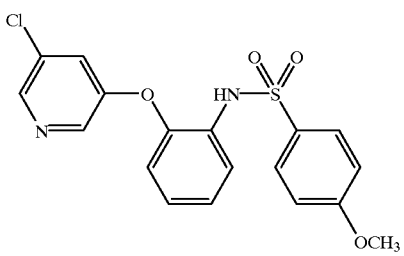

The aniline produced in Example 32.2 (0.41 g) was converted to the title compound using 4-methoxybenzenesulfonyl chloride (0.384 g), in a manner similar to that described in Example 1,.4. The title compound was obtained as a crystalline product (0.28 g) after flash chromatography and trituration with ether. mp 128.5–131° C.

¹H NMR (400 MHz) (CDCl₃) δ 9.965 (s, 1H); 8.311 (d, J=1.8 Hz, 1H); 8.033 (d, J=2.6 Hz, 1H); 7.561 (d, J=8.9 Hz, 2H); 7.456 (dd, J=7.6, 3 Hz, 1H); 7.20 (m, 2H); 7.026 (dd., J=7.4, 3 Hz, 1H); 6.908 (d, J=8.9 Hz, 1H); 6.897 (d, J=3 Hz, 1H); 3.772 (s, 3H).

C₁₈H₁₅N₂ClSO₄ calc: %C 55.32 %H 3.87 %N 7.17 found: %C 55.35 %H 3.82 %N 7.08.

Example 34

This example illustrates the preparation of 1-(3-chloro-5-pyridyloxy)-2-(4-iodobenzenesulfonamido)benzene.

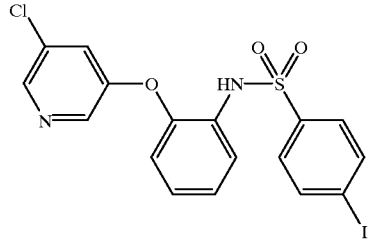

The aniline produced in Example 32.2 (0.4 g) was converted to the title compound using 4-iodobenzenesulfonyl chloride (0.557 g). The title compound was obtained as a crystalline product (0.54 g). mp 168–170° C.

¹H NMR (400 MHz) (CDCl₃) δ 10.170 (s, 1H); 8.332 (d, J=3.1 Hz, 1H); 8.021 (d, J=2.6 Hz, 1H); 7.789 (d, J=7.9 Hz, 2H); 7.42 (m, 1H); 7.394 (d, J=7.9 Hz, 2H); 7.229 (m, 2H); 7.042 (m, ¹H); 6.942 (t, J=1.9 Hz, 1H).

C₁₇H₁₂N₂ClISO₃ calc: %C 41.95 %H 2.49 %N 5.76 found: %C 42.00 %H 2.46 %N 5.73.

Example 35

This example illustrates the preparation of N-(2-furanylmethyl) 5-(2,4-dichloro-5-methylbenzenesulfonamido)-2-(3-chloro-5-pyridyloxy)benzamide.

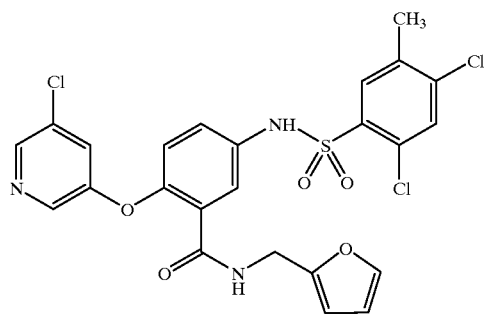

35.1 Preparation of N-(2-furanylmethyl) 2-fluoro-5-nitrobenzamide

To a 0.2M solution of 2-fluoro-5-nitrobenzoic acid (1.0 g, 5.4 mmol, Aldrich) in anhydrous THF at ambient temperature was added furfurylamine (1.1 g, 5.9 mmol), HBTU (2.24g g, 5.9 mmol, Chem-Impex), HOBT (0.8 g, 5:9 imrol, Novabiochem) and NMM (0.59 mL, 5.4 mmol, Aldrich). The resulting solution was stirred for 18 hr. To the reaction mixture was added a 1M solution of aqueous hydrochloric acid (30 mL). The crude mixture was extracted 3× with EtOAc (50 mL). The organic layers were combined, washed one time with a saturated aqueous solution of NaHCO$_3$ (100 mL), one time with brine (100 mL), dried over NaSO$_4$, and concentrated under vacuum to yield 1.4 g (100%) of product as an off white solid which was used without further purification.

$^1$H NMR (400 MHz, DMSO-d$_6$) δ 9.11 (t, J=5.6 Hz, 1H), 8.45–8.35 (m, 2H), 7.67–7.55 (m, 2H), 6.41 (dd, J=3.28, 1.76 Hz, 1H), 6.37 (d, J=2.8 Hz, 1H), 4.5 (d, J=5.8 Hz, 2H).

MS (EI): m/z 264 (15, M+), 263 (100, M-H).

Anal. Calcd for C$_{12}$H$_9$FN$_2$O$_4$: C, 54.55; H, 3.43; N, 10.6. Found: C, 54.74; H, 3.54; N, 10.47.

35.2 Preparation of N2-furanylmethyl) 5-nitro-2-(3-chloro-5-pyridyloxy)benzamide To a 0.08M solution of N-(2-furanylmethyl) 2-fluoro-5-nitrobenzamide (2.64 g, 10 mmol, from Example 35.1) in anhydrous DMSO was added 5-chloro-3-pyridinol (1.36 g, 10.5 mmol, Acros) followed by K$_2$CO$_3$ (1.38 g, 10 mmol). The resulting mixture was stirred at ambient temperature for 1 hr. The crude reaction mixture was diluted with a 1M solution of aqueous hydrochloric acid (125 mL) and extracted 3× with EtOAc (125 mL). The organic layers were combined and washed twice with brine (200 mL), dried over Na$_2$SO$_4$, and concentrated under vacuum to yield 3.7 g (100%) of N-(2-furanylmethyl) 5-nitro-2-(3-chloro-5-pyridyloxy)benzamide as a pale yellow foam which was used without further purification.

$^1$H NMR (400 MHz, DMSO-d$_6$) δ 9.04 (t, J=5.6 Hz, 1H), 8.56 (d, J=1.83 Hz, 1H), 8.48 (d, J=2.2 Hz, 1H), 8.45 (d, J=2.8 Hz, 1H), 8.31 (dd, J=9.2, 2.9 Hz, 1H), 7.88 (dd, J=2.4, 2.2 Hz, 1H), 7.55 (d, J=1.8 Hz, 1H), 7.23 (d, J =9.1 Hz, 1H), 6.38 (dd, J=3.1, 1.9 Hz, 1H), 6.25 (d, J=3.2 Hz, 1H), 4.6 (d, J=5.6 Hz, 2H).

MS (EI): m/z 375 (7, M-H), 374 (38, M-H), 373 (22, M-H), 372 (100, M-H).

35.3 Preparation of N-(2-furanylmethyl) 5-amino-2-(3-chloro-5-pyridyloxy)benzamide To a 0.08M solution of N-(2-furanylmethyl) 5-nitro-2-(3-chloro-5-pyridyloxy)benzamide (3.7 g, 10 mmol, prepared in Example 35.2) in MeOH was added a 50% aqueous slurry of Raney nickel (~6 mL). Hydrogen was then bubbled through the resulting solution for one minute. The resulting mixture was stirred at ambient temperature under one atmosphere of hydrogen for 16 hr. The crude reaction mixture was filtered through a pad of Celite® and the filter cake was washed 3× with MeOH. NOTE: Raney nickel is pyrophoric and should always be kept wet with solvent during the filtration. The Raney nickel can be quenched by adding 6M aqueous HCl. The filtrate was concentrated in the presence of benzene to azeotropically remove water. The residue was purified by chromatography (1–3% MeOH in CH$_2$Cl$_2$) to yield 2.6 g (76%) of N-(2-furanylmethyl) 5-amino-2-(3-chloro-5-pyridyloxy)benzamide as a pale brown solid.

$^1$H NMR (400 MHz, DMSO-d$_6$) δ 8.65 (t, J=5.9 Hz, 1H), 8.28 (d, J=2.2 Hz, 1H), 8.14 (d, J=2.6 Hz, 1H), 7.48 (d, J=1.8 Hz, 1H), 7.22 (dd, J=2.4, 2.0 Hz, 1H), 6.89 (d, J=8.7 Hz, 1H), 6.78 (d, J=2.8 Hz, 1H), 6.69 (dd, J=8.6, 2.7 Hz, 1H), 6.31 (dd, J=3.2, 1.6 Hz, 1H), 6.05 (d, J=3.3 Hz, 1H); 5.33 (s, 2H) 4.29 (d, J =5.9 Hz, 2H).

MS (EI): m/z 347 (11, M+H), 346 (32, M+H), 345 (20, M+H), 344 (100, M+H).

Anal. Calcd for C$_{17}$H$_{14}$ClN$_3$O$_3$: C, 59.4; H, 4.1; N, 12.22; Cl, 10.31. Found: C, 59.45; H, 4.17; N, 12.08; Cl 10.43.

35.4 Preparation of N-(2-furanylmethyl) 5-(2,4-dichloro-5-methylbenzenesulfonamido)-2-(3-chloro-5-pyridyloxy) benzamide To a 0.2M solution of N-(2-furanylmethyl) 5-amino-2-(3-chloro-5-pyridyloxy)benzamide (2.6 g, 7.6 mmol, prepared in Example 35.3) in a 1:1 THF/CH$_2$Cl$_2$ solution was added pyridine (0.67 mL, 8.3 mmol) followed by 2,4-dichloro-5-methylbenzenesulfonyl chloride (2.16 g, 8.3 mmol). The resulting mixture was stirred for 21 hr. A 1M aqueous solution of HCl (100 mL) was add, ed and the crude reaction mixture was extracted 3× with EtOAc (100 mL). The organic layers were combined and washed once with a brine solution (200 mL), dried over Na$_2$SO4, and concentrated under vacuum. The crude solid was purified by chromatography (10–40% EtOAc in hexane) to yield 3.86 g (90%) of product as an off white solid.

Example 36

This example illustrates the preparation of N-ethyl 3-(2, 4-dichloro-5-methylbenzenesulfonamido)-4-(3-chloro-5-pyridyloxy)benzamide.

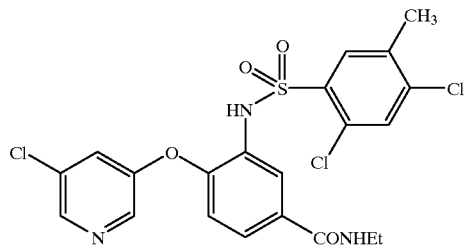

36.1 Preparation of N-ethyl 4-fluoro-3-nitrobenzamide

N-Ethyl 4-fluoro-3-nitrobenzamide was synthesized (100%) in a similar manner as described in Example 35.1, substituting a 2M solution of ethylamine in THF for furfurylamine.

$^1$H NMR (400 MHz, DMSO-d$_6$) δ 8.82 (t, J=4.4 Hz, 1H), 8.62 (dd, J=7.3, 2.4 Hz, 1H), 8.26 (ddd, J=8.3, 6.7, 2.4 Hz, 1H), 7.7 (dd, J=11.1, 8.8 Hz, 1H), 3.3 (pentent, J=7.2 Hz, 2H), 1.15 (t, J=7.3 Hz, 3H).

36.2 Preparation of N-ethyl 3-nitro4-(3-chloro-5-pyridyloxy)benzamide

N-ethyl 3-nitro4-(3-chloro-5-pyridyloxy)benzamide was synthesized (100%) in a similar manner as described in Example 35.2, beginning with N-ethyl 4-fluoro-3-nitrobenzamide.

$^1$H NMR (400 MHz, DMSO-d$_6$) δ 8.78 (t, J=5.3 Hz, 1H), 8.59 (d, J=2.2 Hz, 1H), 8.53 (d, J=2.1 Hz, 1H), 8.48 (d, J=2.3 Hz, 1H), 8.18 (dd, J=8.7, 2.2 Hz, 1H), 7.89 (dd, J=2.2, 2.2 Hz, 1H), 7.42 (d, J=8.6 Hz, H), 3.4–3.2 (m, 2H), 1.14 (t, J=7.2 Hz, 3H).

MS (EI): m/z 325 (8, M+H), 324 (40, M+H), 323 (20, M+H), 322 (100, M+H).

36.3 Preparation of N-ethyl 3-amino-4-(3-chloro-5-pyridyloxy)benzamide

N-ethyl 3-amino-4-(3-chloro-5-pyridyloxy)benzamide was synthesized (100%) in a similar manner as described in Example 35.3, beginning with the product of Example 36.2.

$^1$H NMR (400 MHz, DMSO-d$_6$) δ 8.34 (d, J=2.1 Hz, 1H), 8.28 (t, J=6.4 Hz, 1H), 8.25 (d, J=2.3 Hz, 1H), 7.31 (dd, J=2.5, 2.3 Hz, 1H), 7.03 (dd, J=8.4, 2.1 Hz, 1H), 6.96 (d, J=8.3 Hz, 1H), 5.3 (s, 2H), 3.3 (pentet, J=7.1 Hz, 2H), 1.15 (t, J=7.2 Hz, 3H).

MS (EI): m/z 294 (8, M+H), 292 (23, M+H).

36.4 Preparation of N-ethyl 3-(2,4-dichloro-5-methylbenzenesulfonamido)-4-(3-chloro-5-pyridyloxy)benzamide N-ethyl 3-(2,4dichloro-5-methylbenzenesulfonamido)-4-(3-chloro-5-pyridyloxy)benzamide was synthesized (71%) in a similar manner as described in Example 35.4, beginning with the product of Example 36.3.

$^1$H NMR (400 MHz, DMSO-d$_6$) δ 10.4 (s, 1H), 8.55 (t, J=5.6 Hz, 1H), 8.34 (d, J=2.0 Hz, 1H), 7.99 (d, J=2.5 Hz, 1H), 7.96 (d, J=2.2 Hz, 1H), 7.75 (dd, J=8.5, 2.2 Hz, 1H), 7.74 (s, $^1$H), 7.44 (s, $^1$H), 7.12 (d, J3=8.6 Hz, 1H), 6.95 (dd, J=2.4, 2.2 Hz, 1H), 3.28 (pentet, J=7.2 Hz, 2H), 2.24 (s, 3H), 1.12 (t, J=7.2 Hz, 3H).

MS (EI): m/z 520 (6, M+H), 519 (l0, M+H), 518(40, M+H), 517 (26, M+H), 516 (100, M+H), 515 (25, M+H), 514 (100, M+H).

Example 37

This example illustrates the preparation N-ethyl 2-(2,4-dichloro-5-methylbenzenesulfonamido)-5-(3-chloro-5-pyridyloxy)benzamide.

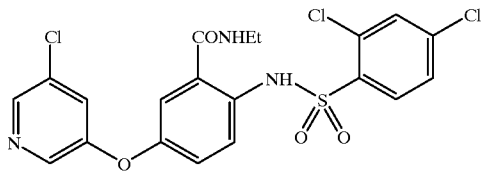

37.1 Preparation of N-ethyl 5-fluoro-2-nitrobenzamide

N-ethyl 5-fluoro-2-nitrobenzamide was synthesized (100%) in a similar manner to the methods described in Example 35.1

$^1$H NMR (400 MHz, DMSO-d$_6$) δ 8.65 (t, J=4.9 Hz, 1H), 8.16 (dd, J=8.8, 4.8 Hz, 1H), 7.57–7.47 (m, 2H), 3.24 (pentent, J 7.2 Hz, 2H), 1.11 (t, J=7.2 Hz, 3H).

MS (EI): m/z 211 (40, M-H).

37.2 Preparation of N-ethyl 2-nitro-5-(3-chloro-5-pyridyloxy)benzamide

N-ethyl 2-nitro-5-(3-chloro-5-pyridyloxy)benzamide was synthesized (100%) in a similar manner to the methods described in Example 35.2.

$^1$H NMR (400 MHz, DMSO-d$_6$) δ 8.62 (t, J=5.4 Hz, 1H), 8.58 (d, J=1.9 Hz, 1H), 8.49 (d, J=2.2 Hz, 1H), 8.12 (d, J=9 Hz, 1H), 7.94 (dd, J=2.4, 2.1 Hz, 1H), 7.3 (dd, J=8.9, 2.7 Hz, 1H), 7.24 (d, J=2.7 Hz, 1H), 3.22 (pentet, J=7.0 Hz, 2H), 1.1 (t, J=7.3 Hz, 3H).

MS (EI): m/z 322 (8, M-H), 320 (20, M-H), 251 (30, M-CONHEt), 249 (100, M-CONHEt).

37.3 Preparation of N-ethyl 2-amino-5-(3-chloro-5-pyridyloxy)benzamide

N-ethyl 2-amino-5-(3chloro-5-pyridyloxy)benzamide was synthesized (88%) in a similar manner to the methods described in Example 35.3.

$^1$H NMR (400 MHz, DMSO-d$_6$) δ 8.32 (d, J=2.0 Hz, 1H), 8.27 (d, J=2.4 Hz, 1H), 8.23 (t, J=5.5 Hz, 1H) 7.36 (dd, J=2.4, 2.0 Hz, 1H), 7.03 (dd, J=8.9, 2.7 Hz, 1H), 6.77 (d, J=8.9 Hz, 1H), 6.46 (s, 2H), 3.6–3.18 (m, 2H), 1.08 (t, J=7.2 Hz, 3H).

MS (EI): m/z 292 (30, M-H), 290 (100, M-H).

37.4 Preparation of N-ethyl 2-(2,4-dichloro-5-methylbenzenesulfonamido)-5-(3-chloro-5-pyridyloxy)benzamide N-ethyl 2-(2,4-dichloro-5-methylbenzenesulfonamido)-5-(3-chloro-5-pyridyloxy)benzamide was synthesized (35%) using methods similar to those described in Example 35.4.

$^1$H NMR (400 MHz, DMSO-d$_6$) δ 12.0 (s, 1H), 8.85 (t, J=4.9 Hz, 1H), 8.42 (d, J=1.9 Hz, 1H), 8.31 (d, J=2.6 Hz, 1H), 8.081(d, J=8.6 Hz, 1H), 7.89 (d, J=2.0 Hz, 1H), 7.65 (dd, J=8.6, 2.1 Hz, 1H), 7.58 (dd, J=2.3, 2.2 Hz, 1H), 7.55 (d, J=2.8 Hz, 1H), 7.43 (d, J=9 Hz, 1H), 7.25 (dd, J=9, 2.8 Hz, 1H), 3.25 (pentet, J=7.2 Hz, 2H), 1.1 (t, J=7.2 Hz,3H).

MS (EI): m/z 503 (10, M-H), 502 (35, M-H), 501 (20, M-H), 500 (100, M-H), 499 (25, M-H), 498 (95, M-H).

Example 38

This example illustrates the preparation of 5-(3-(4-methoxybenzenesulfonamido)phenoxy))-3-chloropyridine and 5-(3-(2,4-dichlorobenzenesulfonamido)phenoxy))-3chloropyridine.

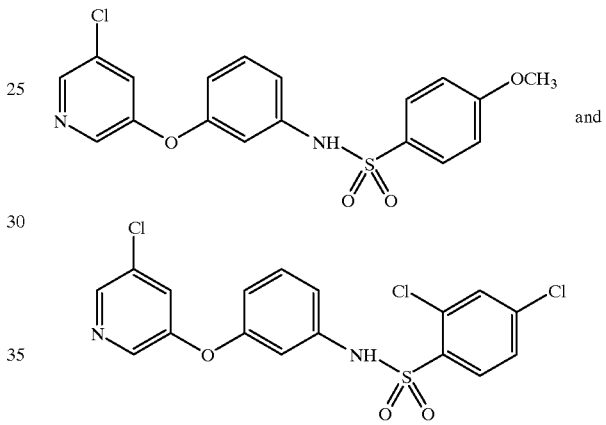

38.1 Preparation of 5-(3-nitrophenoxy)-3-chloropyridine

The title compound was prepared using methods described in U.S. Pat. No. 3,576,616. Briefly, to a 16.5M solution of KOH (2.2 g, 39.6 mmol) in water was added 3-nitrophenol (5 g, 36 mmol) followed by N-methylpyrrolidinone (11 mL) and toluene (3.6 mL). The resulting mixture was heated to 110 ° C. and water was removed azeotropically using a Dean-Stark trap. Excess toluene was removed and collected in the trap followed by the addition of N-methylpyrrolidinone (18 mL) and 3,5dichloropyridine (10.66 g, 72 mmol, Aldrich) and the mixture was stirred for 5 hr at 160 ° C. The temperature was then increased to 200 ° C. and the mixture was stirred for an additional 15 hr. The crude reaction mixture was cooled, water (100 mL) was added followed by EtOAc (100 mL). The mixture was filtered through a pad of Celite®, the phases were separated, and the aqueous phase was extracted 3× with EtOAc (100 mL). The organic phases were combined and washed twice with water (100 mL), once with brine (100 mL), dried over Na$_2$SO$_4$, and concentrated under vacuum. The crude solid was purified by chromatography (10–25% EtOAc in hexanes as eluant) to provide 3.8 g (42%) of product as an orange solid.

$^1$H NMR (400 MHz, DMSO-d$_6$) δ 8.52 (d, J=1. Hz, 1H), 8.41 (d, J=2.4 Hz, 1H), 8.08 (ddd, J=8.2, 2.5, 0.98 Hz, 1H), 7.91 (dd, J=2.4, 2.3 Hz, 1H), 7.83 (dd, J=2.3, 2.2 Hz, 1H), 7.72 (dd, J=8.3, 8.1 Hz, 1H), 7.62 (ddd, J=8.2, 2.5, 0.98 Hz, 1H).

MS (EI): m/z 253 (37, M+H), 251 (100, M+H).

38.2 Preparation of 5-(3-aminophenoxy)-3-chloropyridine 5-(3-Aminophenoxy)-3-chloropyridine was synthesized (100%) in a similar manner as described in Example 35.3.

$^1$H NMR (400 MHz, DMSO-d$_6$) δ 8.38 (d, J=2.2 Hz, 1H), 8.3 (d, J=2.1 Hz, 1H), 7.53 (dd, J=2.3, 2.3 Hz, 1H), 7.02 (dd,;J=8.1, 8.0 Hz, 1H), 6.4 (ddd, J=8.1, 2.1, 1.2 Hz, 1H), 6.24 (dd, J=2.2, 2.2 Hz, 1H), 6.2 (ddd, J=8.0, 2.3, 1.4 Hz, 1H), 5.31 (s, 2H).

MS (El): m/z 223 (37, M+H), 221 (100, M+H).

38.3 Preparation of 5-(3-(2,4-dichlorobenzene-sulfonarnido)phenoxy))-3-chloropyridine 5-(3-(2,4-Dichlorobenzenesulfonamido)phenoxy))-3-chloropyridine was synthesized (70%) in a similar manner as described in Example 35.4.

$^1$H NMR (400 MHz, DMSO-d$_6$) δ 10.91 (s, $^1$H), 8.46 (d, J=1.8 Hz, 1H), 8.26 (d, J=2.6 Hz, 1H), 7.98 (d, J=8.5 Hz, 1H), 7.87 (d, J=1.5 Hz, 1H), 7.6 (dd, J=8.5, 2.2 Hz, 1H), 7.53 (dd, J=2.3, 2.2 Hz, 1H), 7.29 (dd, J=8.4, 8.3 Hz, 1H), 6.94–6.9 (m, $^1$H), 6.8–6.74 (m, 2H).

MS (EI): m/z 435 (5, M+H), 434 (7, M+H), 433 (36, M+H), 432 (20, M+H), 431 (100, M+H), 430 (20, M+H), 429 (90, M+H).

38.4 Preparation of 5-(3-(4-methoxybenzene-sulfonamido)phenoxy))-3-chloropyridine 5-(3-(4-Methoxybenzenesulfonamido)phenoxy))-3-chloropyridine was synthesized (79%) in a similar manner as described in Example 35.4.

$^1$H NMR (400 MHz, DMSO-d$_6$) δ 10.31 (s, $^1$H), 8.45 (d, J=1.8 Hz, 1H), 8.25 (d, J=2.5 Hz, 1H), 7.66 (d, J=8.8 Hz, 2H), 7.53 (dd, J=2.2, 2.2 Hz, 1H), 7.28 (dd, J=9, 7.3 Hz, 1H), 7.06 (d, J=9.0 Hz, 2H), 6.92 (dd, J=8, 1.3 Hz, 1H), 6.79–6.73 (m, 2H), 3.8 (s, 3H).

MS (EI): m/z 395 (5, M+H), 394 (15, M+H), 393 (60, M+H), 392 (30, M+H), 391 (100, M+H).

Example 39

This illustrates the synthesis of 2-(5-chloro-3-pyridyloxy)-5-(2,4-dichlorobenzenesulfonamido)-1-phenylethanone.

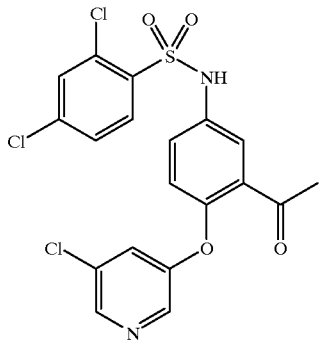

2-Fluoro-5-nitroacetophenone (3.6 g, 20 mmol, described by Cooper, et. al. *J. Med. Chem.* 33:1246–1252 (1990)) and 5-chloro-3-pyridinol (3.2 g, 25 mmol) were dissolved in acetone (20 mL). After addition of solid K$_2$CO$_3$ (3.5 g, 26 mmol), the reaction mixture was heated to reflux for 4 hr. The reaction mixture was cooled and acetone was removed under reduced pressure. The residue was suspended in deionized water (50 mL) and extracted with ethyl acetate (3×50 mL). The combined organic portions were washed with saturated brine, dried over MgSO$_4$, filtered, and concentrated to a brown oil which was partially purified by column chromatography (silica gel, 4:1 hexanes:ethyl acetate) to provide 4 g of 2-(5-chloro-3-pyridyloxy)-5-nitro-1-phenylethanone. This material was dissolved in ethanol (40 mL) and acetic acid (5.3 mL, 93 mmol) to which iron powder (300 mesh, 2.6 g, 46.5 mmol) was added. The reaction mixture was heated to reflux for two days. After removal of excess iron (with a magnetic stir-bar retriever), the reaction mixture was poured into 300 mL of deionized water and extracted with ethyl acetate (3×100 mL). The combined organic portions were washed with saturated brine, dried over MgSO$_4$, filtered, and concentrated to a brown oil which was purified by column chromatography (silica gel, 4:1 hexanes:ethyl acetate). The product 5'-amino-2'-(5-chloro-3-pyridyloxy)-1-phenylethanone was obtained as a yellow oil (1.03g).

MS ESI m/e: 262.9 (M+H)

5'-Amino-2'-(5-chloro-3-pyridyloxy)-1-phenylethanone (100 mg, 0.38 mmol), 2,6-lutidine (49 µL, 0.42 mmol), DMAP (2 mg, 0.019 mmol), and 2,4-dichlorobenzene sulfonyl chloride (103 mg, 0.42 mmol) were combined in CH$_2$Cl$_2$ (2 mL) at room temperature. After 14 h, the reaction mixture was directly purified by radial chromatography (Chromatatron, 2 mm silica gel layer, 2:1 hexanes:ethyl acetate with 0.25% MEOH) to yield the title product as a clear oil which solidified on standing (144 mg).

$^1$H NMR (400 MHz) (CDCl$_3$) δ 8.40 (bs, 1H); 8.25 (bs, $^1$H); 7.96 (d, J=8.6 Hz, 1H); 7.55 (m, 2H); 7.50 (s,1H); 7.25–7.38 (m, 2H); 7.24 (d, J=8.6 Hz, 1H); 6.85 (d, J=6.7 Hz, 1H); 2.54 (s, 3H)

MS ESI m/e: 470.6 (M-H)

Example 40

This example illustrates the synthesis of ethyl 2-(3-chloro-5-pyridyloxy)-5-(2,4-dichlorophenylaminosulfonyl) benzoic acid.

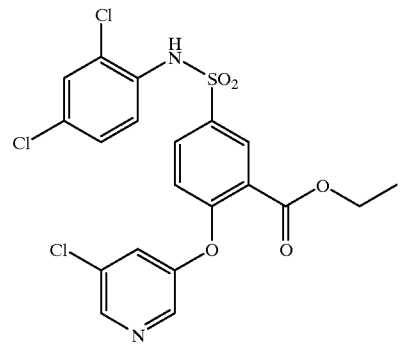

40.1 Preparation of ethyl 2-(3-chloro-5-pyridyloxy)-5-chlorosulfonylbenzoic acid The aniline prepared in Example 1 (250 mg, 0.86 mmol) was converted to the corresponding sulfonyl chloride using the procedures; of R. V. Hoffman (Org. Syn. Coll. Vol. VII, 508–511), to provide 196 mg (61%) of product as a white solid.

MS ESI m/e: 376.0 (M+H).

40.2 Preparation of ethyl 2-(3-chloro-5-pyridyloxy)-5-(2, 4-dichlorophenyl-aminosulfonyl)benzoic acid The sulfonyl chloride prepared above (40 mg, 0.11 mmol), 2,4-dichloroaniline (83 mg, 0.22 mmol), and MeOH (2.0 mL) were combined and stirred at room temperature for 4.0 hr. The reaction mixture was concentrated in vacuo, and the residue was dissolved in CH$_2$Cl$_2$, and washed with 1N aqueous HCl and brine,. The resulting organic solution was dried over MgSO$_4$ and concentrated to give a yellow oil. The crude product was purified using reverse-phase HPLC (C$_{18}$packing, 5–95% CH$_3$CN in H$_2$O). Fractions containing the product were lyophilized to provide 19 mg (36%) of a white solid. mp 153–155 ° C.

$^1$H NMR (400 MHz) (CD$_3$OD) δ 8.35. (1H, d, J=2.0 Hz); 8.20 (2H, d, J=2.4 Hz); 7.91 (1H, dd, J,=8.7 Hz J$_2$=2.4 Hz); 7.55 (1H, d, J=8.7 Hz); 7.45 (1H, dd, J,=4.5 Hz, J$_2$=2.3 Hz); 7.40(1H, d, J=2.3 Hz); 7.35 (1H, dd, J,$_1$=8.7 Hz J$_2$=2.4 Hz); 7.26 (1H, d, J=8.6 Hz); 4.23 (2H, q, J=7.2 Hz); 1.20 (3H, t, J=7.2 Hz).

MS ESI m/e: 501.0 (M+H).

Example 41

This example illustrates the synthesis of ethyl 5-(2, 4dichlorobenzamido)-2-(3-chloro-5-pyridyloxy)benzoate.

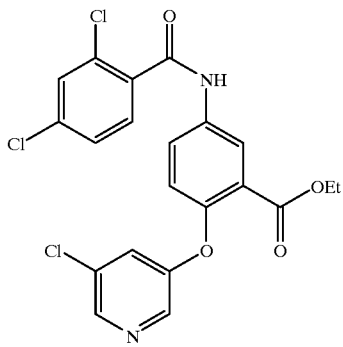

To a solution of the aniline produced.;in Example 1 (100 mg, 0.34 mmol) in CH$_2$Cl$_2$ (2 mL) was added pyridine (81 μL, 1 mmol) and 2,4-dichlorobenzoyl chloride (140 mg, 0.68 mmol). The mixture was stirred for 90 min. The product was purified by column chromatography on silica gel (gradient elution: 30:1 hexane/ethyl acetate to 7:1 hexane/ethyl acetate) followed by recrystallization from CH$_2$Cl$_2$/hexanes to yield 126 mg (79%) of the title compound. mp 125–127° C.

$^1$H NMR (400 MHz) (CD$_3$CN) δ 8.95 (bs, 1H); 8.28 (dd, J=11.4, 2.0 Hz, 2H); 8.20 (d, J=2.4 Hz, 1H); 7.90 (dd, J=8.8, 2.7 Hz, 1H); 7.60 (d, J=8.0 Hz, 2H); 7.46 (dd, J=8.2, 2.0 Hz, 1H); 7.26 (t, J=2.3 Hz, 1H); 7.21 (d, J=8.8 Hz, 1H); 4.19 (q, J=7.2 Hz, 2H); 1.13 (t, J=7.2 Hz, 3H).

MS ESI m/e: 465.0 (M+H)

Example 42

This example illustrates the preparation of 4-(3-chloro-5-pyridyloxy)-3-(4-trifluoromethylbenzenesulfonamido)benzotrifluoride.

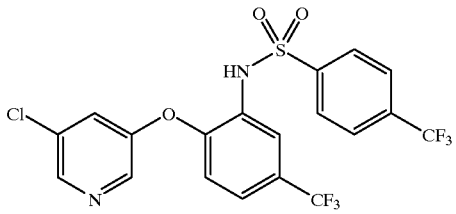

42.1 Preparation of4-(3-chloro-5-pyridyloxy)-3-nitrobenzotrifluoride

Using the method of Example 21.2, 4-fluoro-3-nitrobenzotrifluoride (7.4 g) and 3-chloro-5-hydroxypyridine (4.59 g) were heated with potassium carbonate (5.4 g) in DMF at 80° C. for 1 h, then 60° overnight. Workup gave the title compound (10.9 g) as a yellow solid.

$^1$H NMR (400 MHz) (CDCl$_3$) δ 8.491 (d, J=2 Hz, 1H); 8.359 (d, J=2.8 Hz, 1H); 8.30 (d, J=2 Hz, 1H); 7.847 (dd, J=8.8, 2 Hz, 1H); 7.425 (t, J=2.4 Hz, 1H); 7.185 (d, J=8 Hz, 1H).

42.2 Preparation of4-(3-chloro-5-pyridyl$_1$,oxy)-3-aminobenzotrifluoride

Using the method of Example 17.3, 4-(3-chloro-5-pyridyloxy)-3-nitrobenzotrifluoride (10.9 g) was reduced to the title compound (9.5 g) which was obtained as a light tan solid. mp 117–120° C.

$^1$H NMR (400 MHz) (CDCl$_3$) δ 8.35 (br s, 2H); 7.267 (m, 1H); 7.085 (d, J=1.8 Hz, 1H); 6.922 (dd, J=8.4, 1.4 Hz, 1H); 6.922 (d, J=8.4 Hz, 1H); 3.90 (br s, 2H).

42.3 Preparation of 4-(3-chloro-5-pyridyloxy)-3-(4-trifluoromethyl-benzenesulfonamido)benzotrifluoride Using the method of Example 17.4, i4-(3-chloro-5-pyridyloxy)-3-aminobenzotrifluoride (0.4 g) and 4-trifluoromethylbenzenesulfonyl chloride ((0.339 g ) were combined to provide, after trituration with ether, the title sulfonamide (0.198 g) which was obtained as a crystalline solid. mp 169–171° C.

$^1$H NMR (400 MHz) (DMSO) δ 10.728 (s, 1H); 8.398 (d, J=1.6 Hz, 1H); 8.022 (d, J=2.4 Hz, 1H); 7.916 (d, J=8.4 Hz, 2H); 7.862 (d, J=8.8 Hz, 2H); 7.687 (d, J=2.4 Hz, 1H); 7.59 (dd, J=8.8, 2.4 Hz, 1H); 7.253 (t, J=2.2 Hz, 1H); 7.182 (d, J=8.8 Hz, 1H).

Example 43

This example illustrates the preparation of 4-(3-chloro-5-pyridyloxy)-3-(2,4-dichlorobenzenesulfonamido) benzotrifluoride.

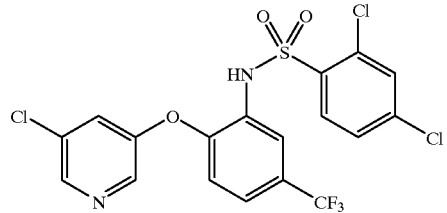

Using the method of Example 17.4, (3chloro-5-pyridyloxy)-3-aminobenzotrifluoride (0.4 g) and 2,4dichlorobenzenesulfonyl chloride ((0.38 g) were combined to provide the title compound (0.26 g), $_1$ a crystalline solid following flash chromatography and trituration with ether. mp 150–151.5° C.

$^1$H NMR (400 MHz) (DMSO) δ 10.767 (s, 1H); 8.415 (d, J=1.8 Hz, 1H); 7.839 (d, J=8.6 Hz, 1H); 7.713 (d, J=1.8 Hz, 1H), 7.64 (d, J=2 Hz, 1H); 7.611 (dd, J=8.7, 1.8 Hz, 1H); 7.499 (dd, J=8.6, 2.1 Hz, 1H); 7.235 (d, J=8.5 Hz, 1H); 7.179 (t, J=2.2 Hz, 1H).

C$_{18}$H$_{10}$N$_2$F$_3$Cl$_3$SO$_3$ calc: %C 43.4 ;%H 2.03 %N 5.63 found: %C 43.62 %H 1.92 %N 5.60.

Example 44

This example illustrates the preparation of 4-(3-chloro-5-pyridyloxy)-3-(4-methoxybenzenesulfonamido) benzotrifluoride.

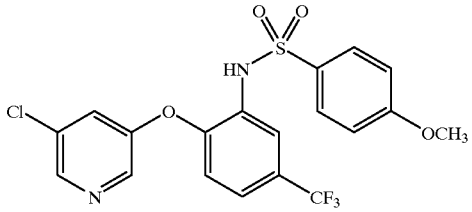

Using the method of Example 17.4, 4(3-chloro-5-pyridyloxy)-3-aminobenzotrifluoride (0.41 g) and 4-methoxybenzenesulfonyl chloride ((0.30 g ) were combined to provide the title compound (0.236 g) as a crystalline solid following flash chromatography and trituration with ether.

$^1$H NMR (400 MHz) (DMSO) δ 10.309 (s, 1H); 8.419 (d, J=2 Hz, 1H); 8.10 (d, J=2.5 Hz, 1H); 7.707 (d, J=2.2 Hz, 1H); 7.613!,(d, J=9 Hz, 2H); 7.527 (dd, J=8.4, 2.2 Hz, 1H); 7.18 (d, J=9.1 Hz, 1H); 7.169 (t, J=2.2 Hz, 1H); 6.978 (d, J=8.9 Hz, 1H); 3.784 (s, 3H).

$C_{19}H_{14}N_2F_3ClSO_4$ calc: %C 49.7 %H 3.08 %N 6.11 found: %C 49.84 %H 3.02 %N 6.11.

Example 45

This example illustrates the preparation of 4-(3-chloro-5-pyridyloxy)-3-(4-iodobenzenesulfonamido) benzotrifluoride.

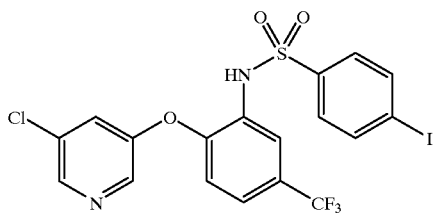

Using the method of Example 17.4, 4-(3-chloro-5-pyridyloxy)-3-aminobenzotrifluoride (0.41 g) and 4-iodobenzenesulfonyl chloride (0.30 g) were combined to provide the title compound (0.34 g) as crystals directly from the reaction mixture. mp 192–193° C.

$^1$H NMR (400 MHz) (DMSO) δ 10.56 (s, 1H); 8.428 (d, J=2.1 Hz, 1H); 8.081 (d, J=2.5 Hz, 1H); 7.847 (d, J=8.5 Hz, 2H); ,7.69 (d, J=2.2 Hz, 1H); 7.569 (dd, J=8.8, 2.2 Hz, 1H); 7.436 (d, J=8.5 Hz, 2R); 7.207 (t., J=2.3 Hz, 1H); 7.204 (d, J=2.4 Hz, 1H).

$C_{18}H_{11}N_2F_3ClSO_3I$ calc: %C 38.9 %H 2.00 %N 05 found: %C 39.14 %H 1.99 %N 5.05.

Example 46

This illustrates the synthesis of 4-(N-oxy-3-chloro-5-pyridyloxy)-3-(2,4-dichlorobenzenesulfonamido) benzotrifluoride.

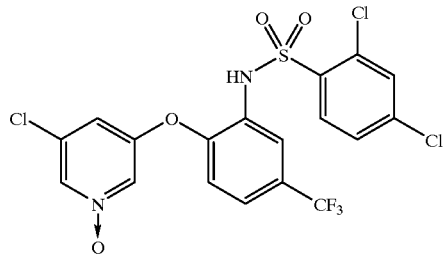

A solution of 4-(3-chloro-5-pyridyloxy)-3-(2,4-dichlorobenzenesulfonamido)-benzotrifluoride from Example 43 in methylene chloride was treated with 3-chloroperoxy-benzoic acid (about 1.2 equiv.) at rt until the reaction was complete. The reaction mixture was concentrated and the solid residue was dissolved in methylene chloride and diluted with hexane to provide the title compound (0.078 g) as a white solid.

$^1$H NMR (400 MHz) (DMSO) δ 10.80 (s, 1H); 8.323 (t, J=1.5 Hz, 1H); 7.868 (d, J=8.6 Hz, 1H); 7.801 (t, J=1.8 Hz, 1H); 7.737 (d, J=2 Hz, 1H); 7.704 (d, J=2.5 Hz, 1H); 7.63 (m, 1H); 7.541 (dd, J=8.7, 2.1 Hz, 1H); 7.396 (d, J=8.5 Hz, if); 6.781 (t, J=1.8 Hz, 1H.

Example 47

This example illustrates the preparation of 2-(3chloro-5-pyridyloxy)-5-(2,4-dichlorobenzenesulfonamido) benzotrifluoride.

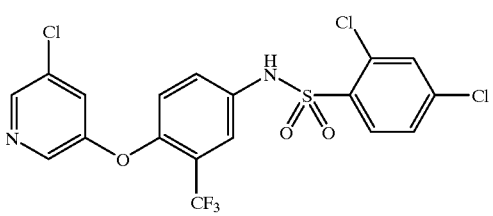

47.1 Preparation of 2-(3-chloro-5-pyridyloxy)7.,5-nitrobenzotrifluoride

Using the method of Example 21.2, 2-fluoro-5-nitrobenzotrifluoride (5.0 g) and 3-chloro-5-hydroxypyridine (3.1 g) were combined with, potassium carbonate (5.4 g) in DMF and heated overnight at 60° C. Workup gave the title compound (8.4 g) as a crude yellow solid which was used directly in the next reaction.

$^1$H NMR (400 Hz) (CDCl$_3$) δ 8.65 (br d, J=2.6 Hz, 1H); 8.558 (br s, 1H); 8.41 (dd, J=9, 2.6 Hz, 1H); 8.403 (br s, 1H); 7.42:(t, J=2.2 Hz, 1H); 7.039 (d, J=9.2 Hz, 1H).

47.2 Preparation of 2-(3-chloro-5-pyridyloxy)-5-aminobenzotrifluoride

Using the method of Example 17.3, 27,(3chloro-5-pyridyloxy)-5-nitrobenzotrifluoride (crude 8.4 g) was reduced to the title compound (7.5 g) which was obtained as an orange oil and used directly in further reactions.

47.3 Preparation of 2-(3-chloro-5-pyridyloxy)-5-(2,4-dichlorobenzene-sulfonamido)benzotrifluoride Using the method of Example 17.4, 2-(3-chloro-5-pyridyloxy)-5-aminobenzotrifluoride (0.394 g) and 2,4-dichlorobenzenesulfonyl chloride (0.34 g) were combined to provide, after flash chromatography and trituration with hexane/ether the title compound as a crystalline solid (0.146 g). mp 129–130° C.

$^1$H NMR (400 MHz) (DMSO) δ 11.124 (s, 1H); 8.452 (d, J=1.8 Hz, 1H); 8.304 (d, J=2.5 Hz, 1H); 8.05 (d, J=8.5 Hz, 1H); 7.91 (d, J=2.1 Hz, 1H); 7.664 (t, J=2.3 Hz, 1H); 7.651 (dd, J=8.8, 2.6 Hz, 1H); 7.476 (d, J.2.6 Hz, 1H); 7.365 (dd, J=8.8, 2.6 Hz, 1H); 7.196 (d, J=8.9 Hz, 1H).

$C_{18}H_{10}N_2F_3Cl_3SO_3$ calc: %C 43.4 %H 2.03 %N 5.63 found: %C 43.35 %H 2.06 %N 5.53.

Example 48

This example illustrates the preparation of 2-(3-chloro-5-pyridyloxy)-5-(4-methylthiobenzenesulfonamido)benzotrifluoride.

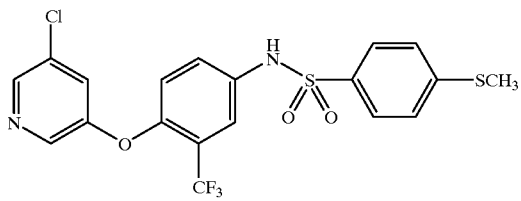

Using the method of Example 17.4, 2-(3Chloro-5-pyridyloxy)-5-aminobenzotrifluoride (0.394 g) and 4-methylthiobenzenesulfonyl chloride (0.34 g) [H. Burton, et al. *J. Chem. Soc.* 1948, 604–605] were combined to provide, after flash chromatography and trituration with hexane/ether, the title compound as crystals (0.22 g). mp 109.5–111° C.

$^1$H NMR (400 Mz) (DMSO) δ 10.603 (s, 1H); 8.451 (br s, 1H); 8.302 (d, J=2.4 Hz, 1H); 7.653 (d, J=8.2 Hz, 2H); 7.467 (d, 3=2.3 Hz, 1H); 7.406 (d, J=8.4 Hz, 2H); 7.361 (dd, J=8.9, 2.5 Hz, 1H); 7.197 (d, J=8.8 Hz, 1H); 2.50 (s, 3H).

Example 49

This example illustrates the preparation of 2-(3-chloro-5-pyridyloxy)-5-(4-methylsulfinylbenzenesulfonamido)benzotrifluoride.

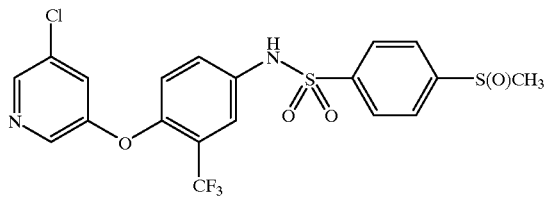

To a solution of 2-(3chloro-5-pyridyloxy)-5-(4-methylthiobenzene-sulfonamido)benzotrifluoride (0.21 g) in acetone (5 mL) was added Oxone™ (0.136 g) in water (1 mL). After 5 hr, the reaction mixture is filtered, and the filtrate is diluted in methylene chloride and extracted with water. The solids from the organic extract were purified by silica chromatography. Trituration with hexane gave the title sulfoxide (0.144 g) as a white solid. mp 156–159° C.

$^1$H NMR (400 MHz) (DMSO) δ 10.73 (s, 1H); 8.46 (d, J=1.8 Hz, 1H); 8.312 (d, J=2.6 Hz, 1H); 7.946 (d, J=8.6 Hz, 2H); 7.891 (d, J=8.2 Hz, 2H); 7.674 (t, J=2.3 Hz, 1H); 7.452 (d, J=2.6 Hz, 1H); 7.39 (dd, J=9.1, 2.6 Hz, 1H); 7.211 (d, J=9.1 Hz, 1H); 2.775 (s, 3H).

$C_{19}H_{14}N_2F_3ClS_2O_4$ calc: %C 46.4 %H 2.87 %N 5.71 found: %C 46.54 %H 2.89 %N 5.64.

Example 50

Using methods similar to Lehmann, et al., ibid., selected compounds exhibited the following $IC_{50}$ values in a PPARγ ligand binding assay utilizing [$^3$H]-BRL 49653 as the radioligand. $IC_{50}$ values are defined as the concentration of test compounds required to reduce by 50% the specific binding of [$^3$H]-BRL 49653.

TABLE

| Compound | $IC_{50}$ (μM) |
|---|---|
| Example 3 | 0.15 |
| Example 4 | 0.3 |
| Example 5 | 0.8 |
| Example 6 | 6 |
| Example 7 | 0.8 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having one of the following formulae:

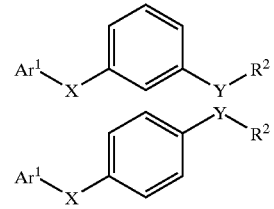

or a pharmaceutically acceptable salt or prodrug thereof, wherein $Ar^1$ is substituted or unsubstituted phenyl;

X is —S(O)$_k$—, wherein the subscript k is an integer of from 0 to 2;

Y is —N(R$^{12}$)—S(O)$_m$—, wherein R$^{12}$ is selected from the group consisting of hydrogen, alkyl, heteroalkyl and arylalkyl and the subscript m is an integer of from 0 to 2; and $R^2$ is a phenyl group substituted with 1–3 substituents selected from the group consisting of halogen and $CF_3$.

2. A compound of claim 1, wherein $R^2$ is a phenyl group substituted with 1–3 halogen substituents.

3. A compound of claim 1, wherein X is —SO$_2$—.

4. A compound of claim 1, wherein X is —S—.

5. A compound of claim 1, wherein Y is —N(R$^{12}$)—S(O)$_2$—.

6. A compound of claim 1, wherein Y is —NH—S(O)$_2$—.

7. A compound of claim 1, wherein X is —SO$_2$— and Y is —NH—S(O)$_2$—.

8. A compound of claim 1, wherein X is —S— and Y is —NH—S (O)$_2$—.

9. A compound of claim 7, wherein $Ar^1$ is substituted with from one to two substituents selected from the group consisting of halogen, —CN, —OCF$_3$, —OH, —O(C$_1$-C$_6$) alkyl, —CF$_3$, (C$_1$-C$_8$)alkyl and —NO$_2$.

10. A compound of claim 7, wherein $Ar^1$ is substituted with from one to two substituents selected from the group consisting of halogen and —CN.

11. A compound of claim 1, having the formula:

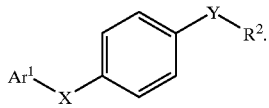

(Ia)

12. A compound of claim 11, wherein X is —SO$_2$—.

13. A compound of claim 11, wherein X is —S—.

14. A compound of claim 11, wherein Y is N(R$^{12}$)—S(O)$_2$—.

15. A compound of claim 11, Wherein Y is —NH—S(O)$_2$—.

16. A compound of claim 11, wherein X is —SO$_2$— and Y is —NH—S(O)$_2$—.

17. A compound of claim 11, wherein X is —S— and Y is —NH—S(O)$_2$—.

18. A compound of claim 11, wherein $Ar^1$ is substituted with from one to two substituents selected from the group consisting of halogen, —CN, —OCF$_3$, —OH, —O(C$_1$-C$_6$)alkyl, —CF$_3$, (C$_1$-C$_8$)alkyl and —NO$_2$.

19. A compound of claim 11, wherein $Ar^1$ is substituted with from one to two substituents selected from the group consisting of halogen and —CN.

20. A compound of claim 11, wherein X is —SO$_2$— and Y is —NH—S(O)$_2$— and $Ar^1$ is substituted with from one to two substituents selected from the group consisting of halogen and —CN.

21. A compound of claim 1, having the formula:

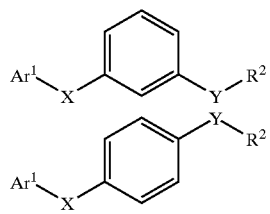

22. A pharmaceutical composition comprising a pharmaceutically acceptable carrier or excipient and a compound having one of the following formulae:

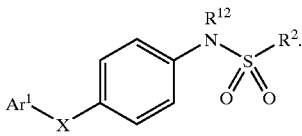

wherein $Ar^1$ is substituted or unsubstituted phenyl;

X is —S(O)$_k$—, wherein the subscript k is an integer of from 0 to 2;

Y is —N(R$^{12}$)—S(O)$_m$—, wherein R$^{12}$ is selected from the group consisting of hydrogen, alkyl, heteroalkyl and arylalkyl and the subscript m is an integer of from 0 to 2; and $R^2$ is a phenyl group substituted with 1–3 substituents selected from the group consisting of halogen and CF$_3$.

23. A method for modulating conditions associated with metabolic or inflammatory disorders in a host, said method comprising administering to said host an efficacious amount of a compound having one of the following formulae:

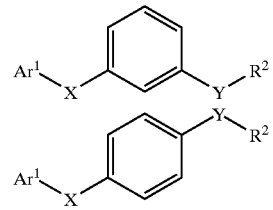

wherein $Ar^1$ is substituted or unsubstituted phenyl;

X is —S(O)$_k$—, wherein the subscript k is an integer of from 0 to 2;

Y is —N(R$^{12}$)—S(O)$_m$—, wherein R$^{12}$ is selected from the group consisting of hydrogen, alkyl, heteroalkyl and arylalkyl and the subscript m is an integer of from 0 to 2; and R2 is a phenyl group substituted with 1–3 substituents selected from the group consisting of halogen and CF$_3$.

24. A method in accordance with claim 23, wherein said host is a human.

25. A method in accordance with claim 23, wherein said administering is oral.

26. A method in accordance with claim 23, wherein said administering is topical.

27. A method in accordance with claim 23, wherein said administering is parenteral.

28. A method in accordance with claim 23, wherein said administering is prophylactic to prevent the onset of a PPARγ-mediated condition.

29. A method in accordance with claim 23, wherein said disorders are selected from the group consisting of NIDDM, obesity and inflammatory conditions.

30. A method in accordance with claim 23, wherein said metabolic disorders are mediated by PPARγ.

31. The compound of claim 1, wherein the compound is a PPARγ receptor modulator.

32. The pharmaceutical composition of claim 22, wherein the compound is a PPARγ receptor modulator.

33. The method of claim 23, wherein the compound is a PPARγ receptor modulator.

* * * * *